US012589109B2

(12) United States Patent
Haldar et al.

(10) Patent No.: US 12,589,109 B2
(45) Date of Patent: Mar. 31, 2026

(54) THERAPY TO STIMULATE HIPPOCAMPAL NEURAL PROGENITORS AND ADULT NEUROGENESIS

(71) Applicant: UNIVERSITY OF NOTRE DAME DU LAC, South Bend, IN (US)

(72) Inventors: Kasturi Haldar, South Bend, IN (US); Md. Suhail Alam, South Bend, IN (US); Arpitha Mysore Rajashekara, South Bend, IN (US)

(73) Assignee: UNIVERSITY OF NOTRE DAME DU LAC, South Bend, IN (US)

( * ) Notice: Subject to any disclaimer, the term of this patent is extended or adjusted under 35 U.S.C. 154(b) by 491 days.

(21) Appl. No.: 18/043,377

(22) PCT Filed: Sep. 3, 2021

(86) PCT No.: PCT/US2021/049079
§ 371 (c)(1),
(2) Date: Feb. 28, 2023

(87) PCT Pub. No.: WO2022/051631
PCT Pub. Date: Mar. 10, 2022

(65) Prior Publication Data
US 2023/0310490 A1 Oct. 5, 2023

Related U.S. Application Data

(60) Provisional application No. 63/074,201, filed on Sep. 3, 2020.

(51) Int. Cl.
*A61K 31/724* (2006.01)
*A61K 31/08* (2006.01)
*A61P 25/28* (2006.01)

(52) U.S. Cl.
CPC ............ *A61K 31/724* (2013.01); *A61K 31/08* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 10,413,517 B2 | 9/2019 | Haldar et al. | |
| 10,597,696 B2 | 3/2020 | Haldar et al. | |
| 11,219,608 B2 | 1/2022 | Apkarian et al. | |
| 2015/0359762 A1 | 12/2015 | Haldar et al. | |
| 2018/0110798 A1 | 4/2018 | McKew et al. | |
| 2020/0000840 A1 | 1/2020 | Wittkowski | |
| 2020/0054629 A1 | 2/2020 | Tran | |
| 2020/0179313 A1 | 6/2020 | Haldar et al. | |

FOREIGN PATENT DOCUMENTS

| | | |
|---|---|---|
| WO | 2016168772 A1 | 10/2016 |
| WO | 2017163128 A3 | 11/2017 |
| WO | 2019219741 A1 | 11/2019 |
| WO | 2020092107 A1 | 5/2020 |

OTHER PUBLICATIONS

Nusca et al., "A marked paucity of granule cells in the developing cerebellum of the Npc1−/− mouse is corrected by a single injection of hydroxypropyl-β-cyclodextrin" Neurobiology of Disease, vol. 70 pp. 117-126, DOI:10.1016/j.nbd.2014.06.012 (Year: 2014).*

"Kabuki Syndrome", downloaded from my.clevelandclinic.org (Year: 2025).*

Montfort et al., "Follow-Up Study of Growth Hormone Therapy in Children with Kabuki Syndrome: Two-Year Treatment Results" Hormone Research in Pediatrics vol. 94 pp. 285-296, DOI: 10.1159/000519963 (Year: 2021).*

Alam et al., "Chronic administration of an HDAC inhibitor treats both neurological and systemic Niemann-Pick type C disease in a mouse model", Sci Transl Med., 8(326):326ra23, Feb. 2016.

Aqul et al., "Unesterified Cholesterol Accumulation in Late Endosomes/Lysosomes Causes Neurodegeneration and is Prevented by Driving Cholesterol Export from This Compartment", J. Neurosci. 31, 9404-9413, Jun. 2011.

International Search Report and Written Opinion of the ISA/US in PCT/US2021/049079, dated Dec. 23, 2021, 8pgs.

Jarazo et al., "Parkinson's Disease Phenotypes in Patient Neuronal Cultures and Brain Organoids Improved by 2-Hydroxypropyl-β-Cyclodextrin Treatment," Mov Disord., Oct. 2021, 16pgs.

Liu et al., ", Reversal of defective lysosomal transport in NPC disease ameliorates liver dysfunction and neurodegeneration in the npc1−/− mouse", Proc. Natl. Acad. Sci. U.S.A., 106(7):2377-82, Feb. 2009.

Petrik et al., "Functional and Mechanistic Exploration of an Adult Neurogenesis-Promoting Small Molecule," FASEB J., 26(8):3148-3162, Aug. 2012.

Yergey et al., "Characterization of Hydroxypropyl-Betacyclodextrins Used in the Treatment of Niemann-Pick Disease Type C1," PLoS One, 12(4):e0175478, Apr. 2017.

Extended Search Report and Written Opinion of the European Patent Office dated Jul. 5, 2024 in EP Application No. 21865199.0; 9pgs.

* cited by examiner

*Primary Examiner* — Andrea Olson

(74) *Attorney, Agent, or Firm* — Haukaas Fortius PLLC; Michael H. Haukaas; Paul K. Judd

(57) ABSTRACT

Aspects of the invention are directed to methods of stimulating or promoting neurogenesis by administering to a subject of a composition comprising a cyclodextrin and a polyethylene glycol to alleviate learning, memory and cognitive deficits present in subjects afflicted with various brain disorders or from neurodegenerative disorder associated with aging.

17 Claims, 15 Drawing Sheets a

*Kmt2d*⁺ᐟᵝᴳᵉᵒ mouse model b a b a

WT-Untreated b

Kbk-Untreated c                                Kbk-Drug d a

WT, PEG b

WT, DCF

THERAPY TO STIMULATE HIPPOCAMPAL NEURAL PROGENITORS AND ADULT NEUROGENESIS

RELATED APPLICATIONS

This application is a National Stage filing under 35 U.S.C. § 371 of International Application No. PCT/US2021/049079, filed Sep. 3, 2021 which claims the benefit of U.S. Provisional Patent Application No. 63/074,201 filed Sep. 3, 2020, which applications are incorporated herein by reference.

BACKGROUND OF THE INVENTION

The loss of neurons in the adult human brain—such as it occurs in aging humans and in neurological disorders—is an irreversible process. Additionally, many major diseases of the human brain involve deficiencies of certain neuron populations. The inability by the adult human brain to generate replacement cells is thought to be a leading cause for the irreversible and progressive nature of several neurological diseases and may be responsible for persistent and ongoing impairment. In most regions of the brain, the neuron generation is generally confined to a discrete developmental period. Once this developmental period ceases, it believed that no further generation of neuronal cells occurs in the living human brain.

One neurological disease is Kabuki syndrome (KS). KS is a multi-system disorder that compromises regulatory mechanisms underlying hypoxia. Varying degrees of intellectual disability appear to be associated with the majority of patients. KS is also associated with defects in hippocampal function in the brain, facial dysmorphisms, and immunological responses. Furthermore, KS is associated with defects in cardiac and immunological conditions as well as post-natal neurogenesis and reduced granule cells in the hippocampus (and loss of hippocampal functions of learning and memory). Liver conditions are reported, but not consistently so in patients. Hippocampal function is needed for intellectual functions of cognition, learning and memory as well as tactile allodynia. The loss of these capacities post-weaning in KS mice, presents KS as a monogenetic disorder to query post-natal hippocampal function and intellectual disability.

As it stands, there are no known treatments that stimulate post-natal hippocampal functions of memory, cognition, tactile allodynia, and over all intellectual disability, as well as treatments that stimulate long term, hippocampal post-natal neurogenesis and growth of granule cell neurons. Accordingly, there is a need for methods of stimulating neurogenesis in aged subjects or those suffering from a neurodegenerative disorder such as KS. The present disclosure satisfies theses needs.

SUMMARY OF THE INVENTION

Hippocampal development is required for brain function and occurs in embryonic, perinatal and post-natal stages. The hippocampus is a major brain region in humans. It is part of the limbic system and important for learning and memory. Studies in mice confirm this role and suggest a function in mechanical sensory systems. Hippocampal function is needed for learning and memory and tactile allodynia. A mouse model with impaired hippocampal function was used to develop a treatment that stimulates post-natal hippocampal function with potential to support brain functions of cognition, learning, memory, tactile allodynia, and overall intellectual disability. Treatment was also found to stimulate proliferation of neural precursors and neurogenesis in hippocampi lacking genetic defects, suggesting broad applicability to a wide range of neurological and neurodegenerative conditions where the pathway is not impaired.

Accordingly, the present disclosure provides methods and compositions comprising compounds useful for stimulating neurogenesis and post-natal hippocampal function in subjects having, for example, a brain injury, a neurological disorder, or in subjects having no known brain injury of neurological disorder. One embodiment provides a method for stimulating neurogenesis in a subject comprising of administering to the subject a therapeutically effective amount of a composition comprising a cyclodextrin present in an amount of about 13% w/w to about 45% w/w and a polyethylene glycol (PEG) present in an amount of greater than 8% w/w, thereby stimulating neurogenesis, the neurogenesis comprising at least a 20% increase in doublecortin (DCX) positive neuroblast cells in the subgranular zone of the dentate gyrus of the hippocampus that mature into neurons as compared to an untreated subject. Optionally, the composition also may comprise a pharmaceutically acceptable carrier.

In some embodiments, neurogenesis may be characterized by an increase of about 20% in doublecortin (DCX positive) expressing neurons compared to the number of DCX positive neurons of untreated subjects. In other embodiments, neurogenesis may be characterized by one or more of a 3-fold to 4-fold increase in Sox2 expression, a 1-fold to 2-fold increase in Sox4 expression, a 1-fold to 3.5-fold increase in Nestin expression, or a 1-fold to 2.5-fold increase in DCX expression, in neural progenitor cells in treated subjects compared to subjects treated only with PEG and dimethyl sulfoxide (DMSO).

In another embodiment, a method for stimulating neurogenesis in a subject comprises administering to the subject a therapeutically effective amount of a composition consisting of about 13% to about 45% w/w cyclodextrin and greater than 8% w/w of a polyethylene glycol (PEG), thereby stimulating neurogenesis.

In another embodiment, a method for stimulating neurogenesis in a subject comprises administering to the subject a therapeutically effective amount of a composition consisting of about 13% to about 45% w/w cyclodextrin, greater than 8% w/w of a polyethylene glycol (PEG), and a pharmaceutically acceptable carrier, thereby stimulating neurogenesis.

In another embodiment, a method for stimulating neurogenesis in a subject comprises administering to the subject a therapeutically effective amount of a composition consisting of about 13% to about 45% w/w 2-hydroxypropyl-β-cyclodextrin (HPBCD) and greater than 8% w/w PEG-400, thereby stimulating neurogenesis.

In another embodiment, a method for stimulating neurogenesis in a subject comprises administering to the subject a therapeutically effective amount of a composition consisting of about 13% to about 45% w/w 2-hydroxypropyl-β-cyclodextrin (HPBCD), and greater than 8% w/w PEG-400, and a pharmaceutically acceptable carrier, thereby stimulating neurogenesis.

Also provided are methods for treating intellectual disability in Kabuki syndrome in a subject in need thereof comprise steps of administering to the subject a therapeutically effective amount of a composition consisting of 2-hydroxypropyl-β-cyclodextrin (HPBCD) and PEG-400, or 2-hydroxypropyl-β-cyclodextrin (HPBCD), PEG-400, and a pharmaceutically acceptable carrier, thereby treating intellectual disability in Kabuki syndrome.

The disclosure also provides for compositions for stimulating neurogenesis comprising about 13% to about 45% w/w cyclodextrin and greater than 8% w/w polyethylene glycol (PEG). In other embodiments, a composition for use in stimulating neurogenesis comprises about 25% to about 45% w/w of a cyclodextrin, or about 40% w/w 2-hydroxypropyl-β-cyclodextrin (HPBCD), and about 20% to about 45% w/w polyethylene glycol-400 (PEG-400). In some embodiments, the composition excludes other active agents.

These and other features and advantages of this invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

(c) Percentage increase in EdU high nuclei after treatment with PEG and DMSO, and DCF (HPBCD in PEG and DMSO). EdU stains newly synthesized DNA and is indicative of cell proliferation.

Figure 9:
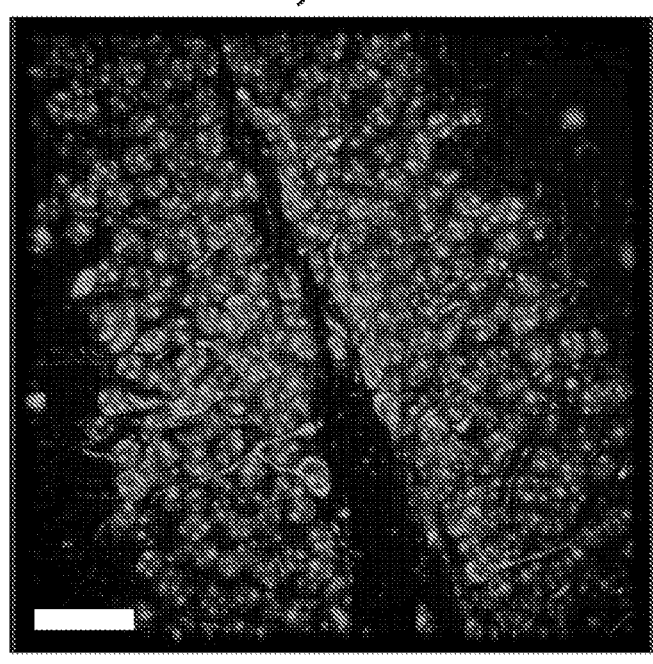
Figure 9:
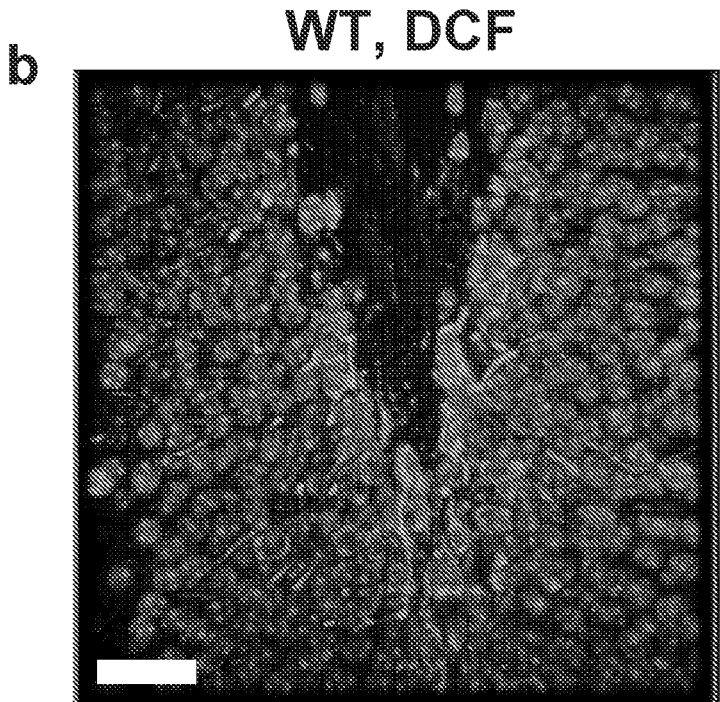
Figure 9:
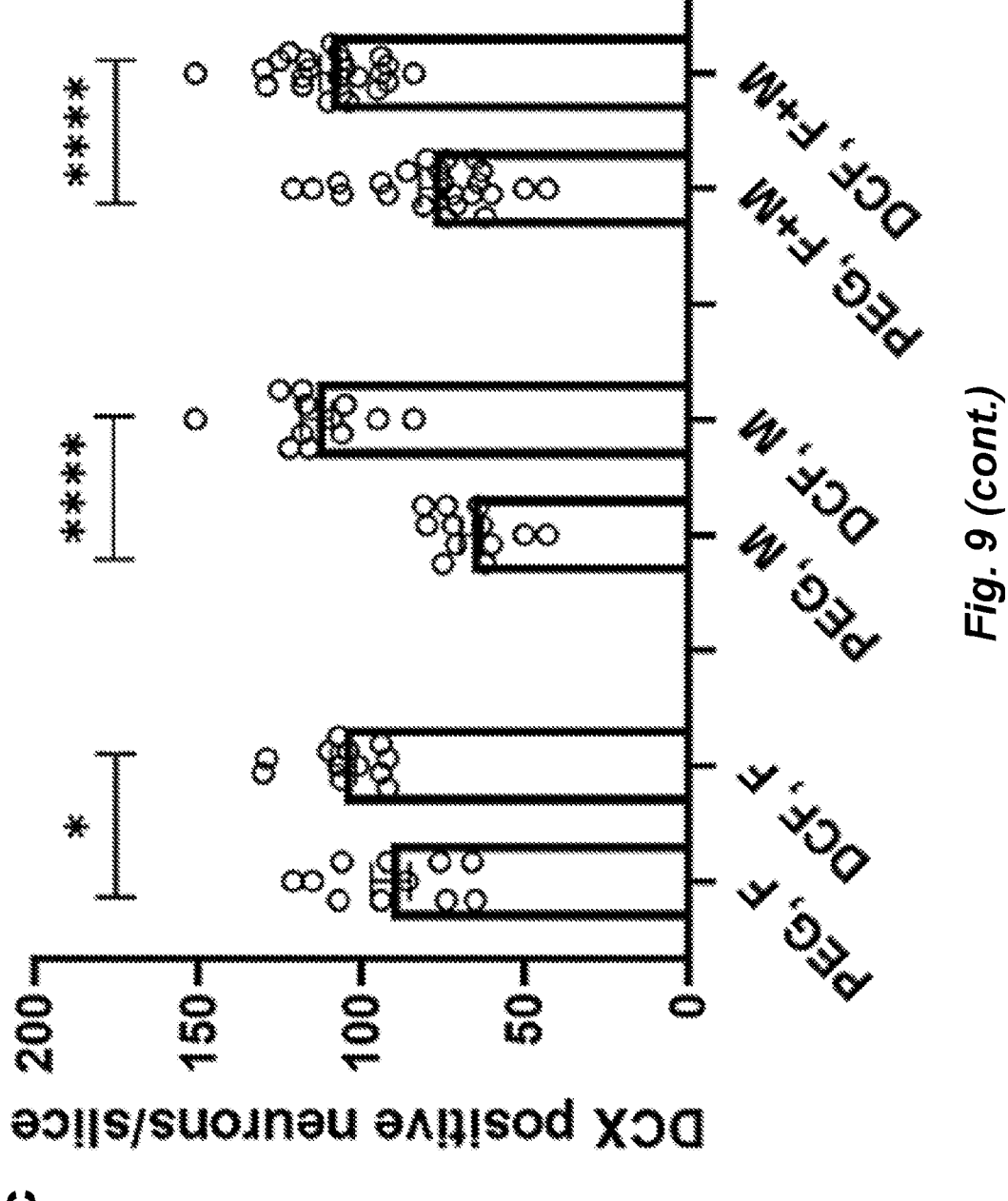

FIG. 9. Administration of DCF in WT mice increases DCX-positive neuroblasts in the subgranular zone (SGZ). DCF induces hippocampal neurogenesis independent of genetic defect. (a), WT mice treated with PEG and DMSO. Neuroblast cells are stained for DCX and appear as light grey cells emerging in the subgranular zone of the dentate gyrus in this application). (b) WT mice treated with DCF (HPBCD in PEG and DMSO) WT mice treated with DCF show increased staining of neuroblast cells per slice in the SGZ compared to PEG/DMSO alone. (c) Quantification of DCX-positive neurons/slice in Females, Males, and both. WT mice injected once weekly starting at P21-P30; analyzed at 60-70 days of age; N=4/group (2M, 2F); DCX-positive cells were counted at 5-6 different depths. Scale bar, 25 μM.

Figure 10:
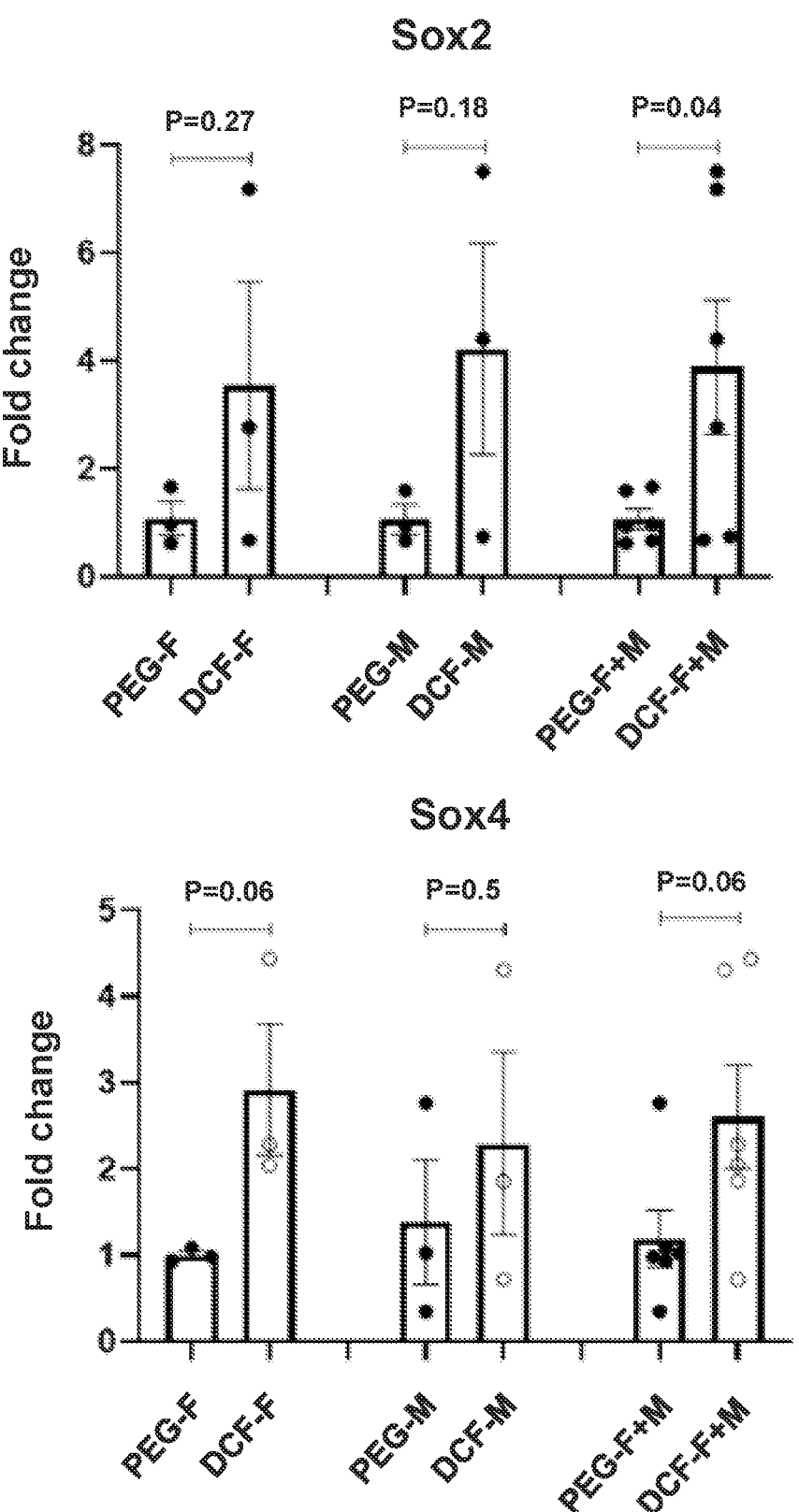
Figure 10:
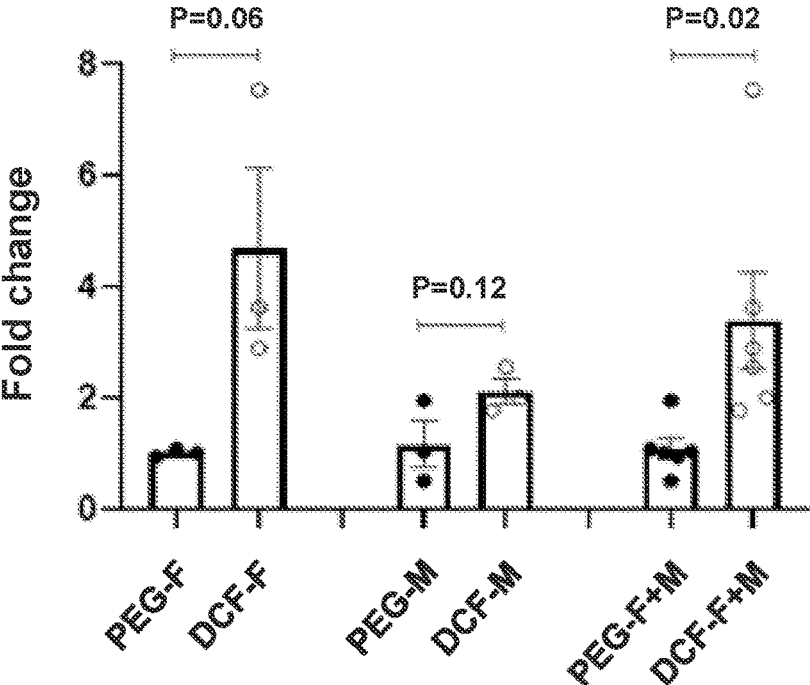
Figure 10:
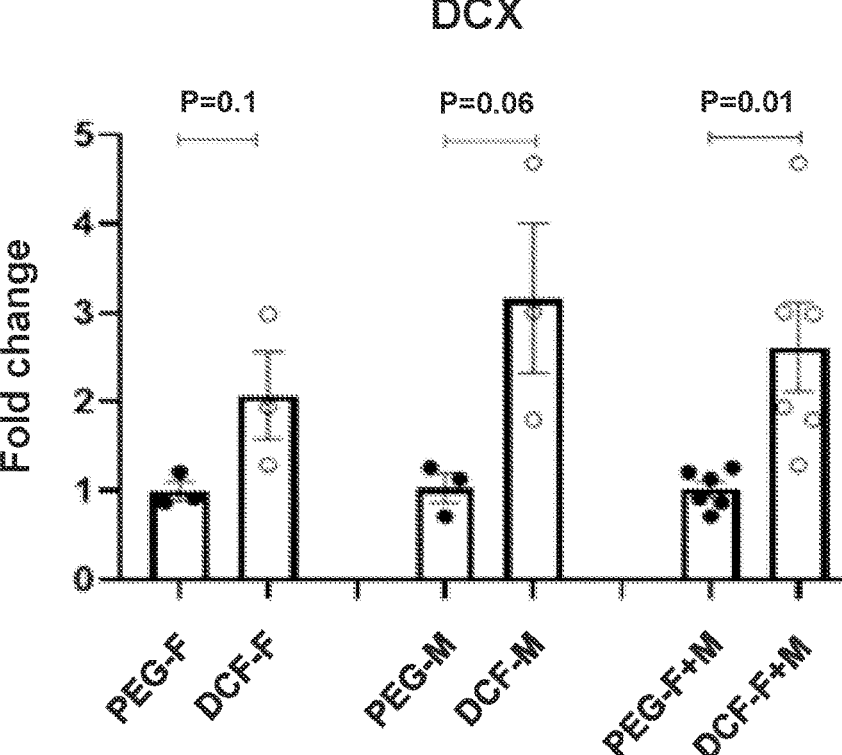

FIG. 10. Quantitative PCR analysis of indicated neurogenesis markers in hippocampus of WT mice injected with DCF (HPBCD in PEG and DMSO) or PEG (PEG and DMSO) Injections started weekly at P21-P23, analysis performed at 2 months of age. N=6 (3M+3F). Markers of neurogenesis used Nestin, Sox 2,Sox 4 and DCX, show that DCF induces proliferation of neural precursor cells that mature to young neurons in normal animals.

Figure 11:
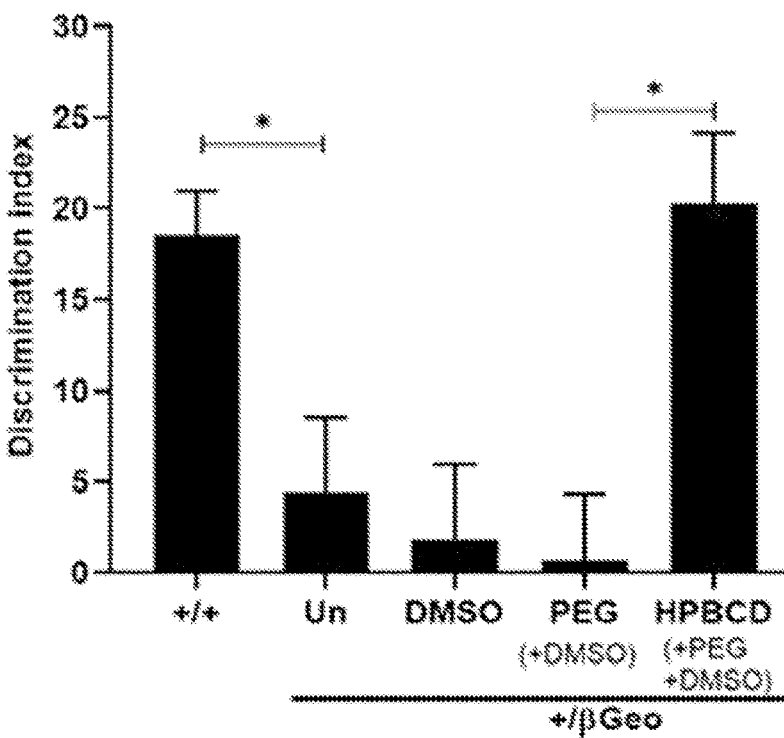

FIG. 11. Effect of DCF and its components on hippocampal learning and memory, nociception and neurogenesis. Discrimination index (DI) determined using the NOR assay to assess hippocampal function of learning and memory of $Kmt2d^{+/\beta Geo}$ mice treated with DCF or its components as indicated. Mice were assessed at 5-7 months of age. Numbers of mice in different groups are, $Kmt2d^{+/+}$ (+/+, n=25, 12F, 13M), $Kmt2d^{+/\beta Geo}$ left un-injected (un, n=24, 10F, 14M) or injected with DMSO (n=10, 5F, 5M), PEG with DMSO (n=12, 6F, 6M), or HPBCD in PEG and DMSO (n=20, 11F, 9M). Data are mean±SEM, one-way analysis of variance (ANOVA) with Tukey's posthoc test.

Figure 12:
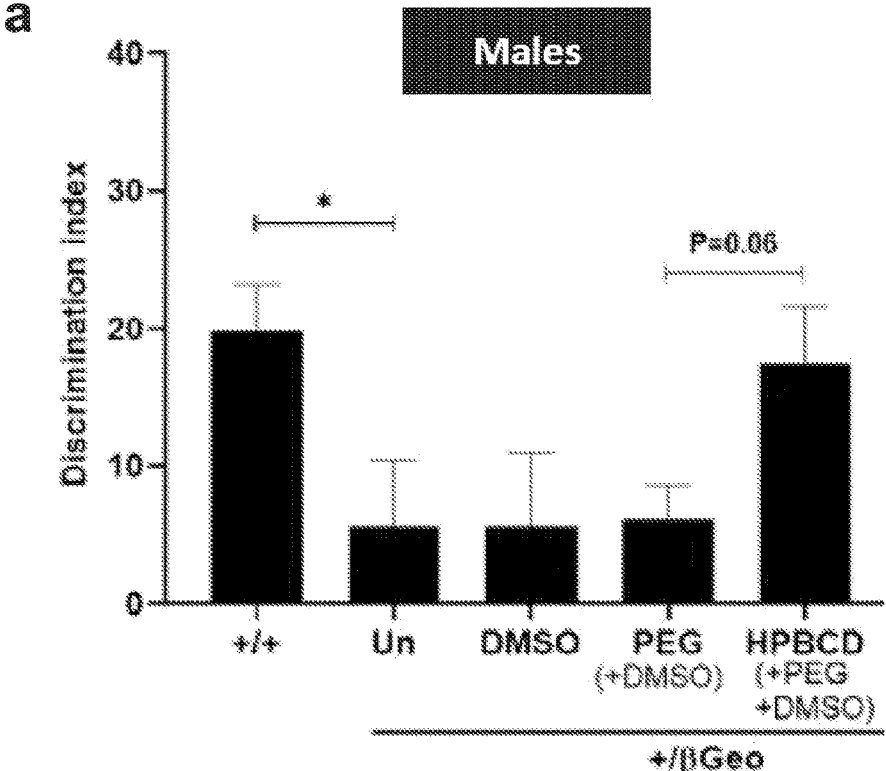
Figure 12:
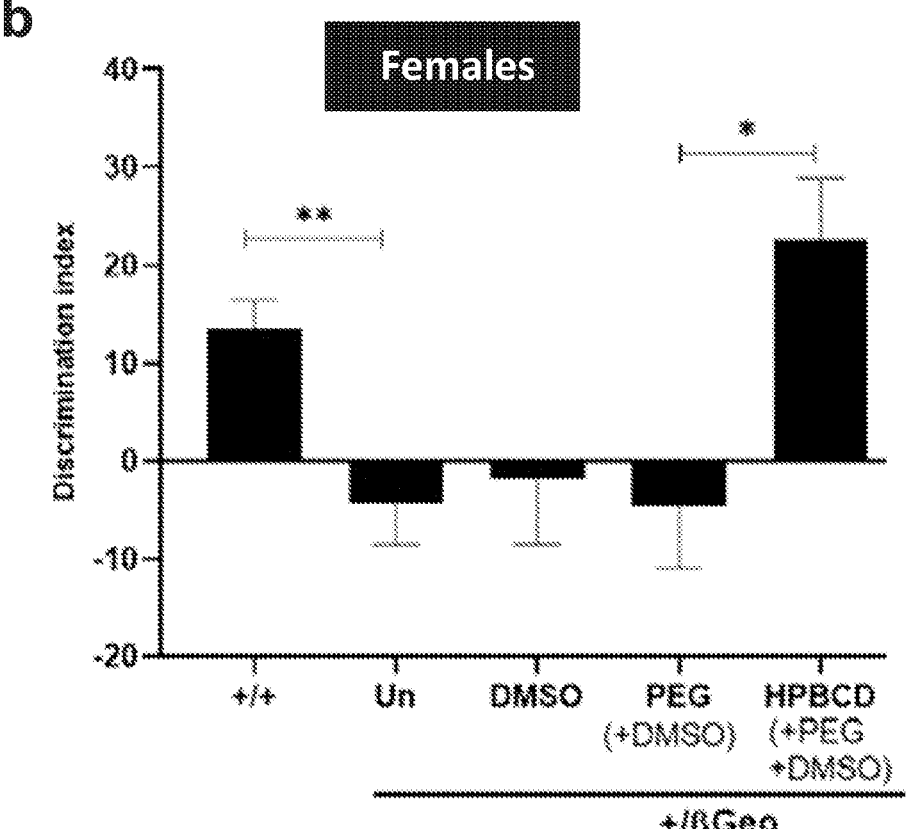

FIG. 12. Gender-based analysis of learning and memory of drug-treated $Kmt2d^{+/\beta Geo}$ mice. Bar diagrams show discrimination index (DI) determined by novel object recognition assay in (a) male (b) female mice. $Kmt2d^{+/\beta Geo}$ were left untreated (Un) or given weekly i.p injections of DCF or its components as indicated starting at P21-P23 and assessed at 5-7 months of age. $Kmt2d^{+/+}$ served as healthy control. Number of mice are, untreated $Kmt2d^{+/+}$ (+/+) males (n=13), females (n=12); untreated $Kmt2d^{+/\beta Geo}$ males (n=14), females (n=10); $Kmt2d^{+/\beta Geo}$ DMSO males (n=5), females (n=5F); $Kmt2d^{+/\beta Geo}$ PEG in DMSO, males (n=6), females (n=6); and $Kmt2d^{+/\beta Geo}$ HPBCD in PEG and DMSO, males (n=9), females (n=11). Data are mean±SEM. Statistical analysis by Student's t-test. *P<0.05, **P<0.01.

DETAILED DESCRIPTION OF THE INVENTION

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Con-*

*densed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

Alternatively, the terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the compositions, the type or extent of supplemental therapy used, ongoing disease process and type of treatment desired (e.g., aggressive vs. conventional treatment).

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

As used herein, "subject" or "patient" means an individual having symptoms of, or at risk for, a disease or other malignancy. A patient may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

The compositions described herein may be administered with additional compositions to prolong stability and activity of the compositions, or in combination with other therapeutic drugs.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

As used herein, the term "tactile allodynia" is a neurological condition in which pain, including severe pain, may occur with a light touch of the skin.

EMBODIMENTS OF THE INVENTION

Hippocampal development is required for brain function and occurs in embryonic, perinatal and post-natal stages. The hippocampus—a major brain region in humans—is part of the limbic system and important for learning and memory. Studies in mice confirm this role and suggest a function in mechanical sensory systems. A mouse model of Kabuki Syndrome with impaired hippocampal function was used to develop a treatment that boosts hippocampal neural progenitors and adult neurogenesis, increases post-natal learning, memory, and controls mechanosensitive tactile responses in, for example, subjects having neural diseases or defects, and in particular, having Kabuki syndrome.

Accordingly, this disclosure provides for compositions and methods of use for stimulating neurogenesis in a subject, including intellectual disability caused by neurodegenerative disease, brain injury, nerve injury, psychiatric disorders, or aging, comprising, consisting essentially of, or consisting of administering to the subject a therapeutically effective amount of a composition comprising a cyclodextrin and a polyethylene glycol (PEG), thereby stimulating neurogenesis.

In certain embodiments, a method for stimulating neurogenesis in a subject, comprises, consists essentially of, or consists of administering to the subject a therapeutically effective amount of a composition comprising a cyclodextrin, a polyethylene glycol (PEG), and a pharmaceutically acceptable carrier, thereby stimulating neurogenesis.

In some embodiments, the cyclodextrin includes one or more of hydroxypropyl-β-cyclodextrin, 2-hydroxypropyl-β-cyclodextrin, dimethyl-β-cyclodextrin, hydroxypropyl-α-cyclodextrin, hydroxypropyl-γ-cyclodextrin, or any combination thereof. In some embodiments, the cyclodextrin is β-cyclodextrin. In some embodiments, the cyclodextrin is hydroxypropyl-β-cyclodextrin. In some embodiments, the cyclodextrin is 2-hydroxypropyl-β-cyclodextrin.

The cyclodextrin may have any average molecular weight ranging, for example from about 970 to 6,000 Da depending, for example, on the type of cyclodextrin (α, β, or γ) and whether it is crosslinked or uncrosslinked, substituted or unsubstituted, the degree of substitution, and the like, as is known in the art. Accordingly, the cyclodextrin may be crosslinked or uncrosslinked, substituted or unsubstituted, or any combination thereof. Referring to the molecular weight, the aforementioned range includes all values and subranges therebetween, including about 970, 972, 980, 990, 1000, 1010, 1030, 1050, 1070, 1090, 1100, 1120, 1140, 1160, 1180, 1200, 1250, 1300, 1350, 1370, 1380, 1390, 1395, 1400, 1410, 1420, 1430, 1440, 1460, 1480, 1500, 1600, 1800, 2000, 2500, 3000, 3500, 4000, 5000, 6000 Da, or combination thereof. In some embodiments, the cyclodextrin is 2-hydroxypropyl-β-cyclodextrin and may have an average molecular weight of about 900 to about 1500, or about 1000 to about 1450, or about 1200 to about 1450, or about 1396 Da. In some embodiments, the cyclodextrin is α-cyclodextrin and may have an average molecular weight of about 900 to about 1000 Da, or about 973 Da. In some embodiments, the cyclodextrin is β-cyclodextrin and may have a molecular weight of about 1000 to about 1200, or about 1135 Da. In some embodiments, the cyclodextrin is γ-cyclodextrin and may have a molecular weight of about 1200 to about 1350, or about 1297 Da.

If substituted, the cyclodextrin may have a degree of substitution, or average number of substituents per glucopyranose unit, ranging from 0.5 to 3. This range includes any value or subrange therebetween, including 0.5, 0.55, 0.6, 0.65, 0.7, 0.75, 0.8, 0.85, 0.9, 0.95, 1, 1.1, 1.2, 1.3, 1.4, 1.5, 1.6, 1.7, 1.8, 1.9, 2, 2.2, 2.4, 2.5, 2.6, 2.7, 2.8, 2.9, 3, or any combination thereof.

The cyclodextrin is preferably water soluble. The cyclodextrin may have a water solubility at 25° C. of about 10 mg/mL or greater. This range includes all values and subranges therebetween, including about 10, 20, 40, 60, 100, 200, 300, 400, 500, 600 mg/mL, or greater. Mixtures of different cyclodextrins are possible. In some embodiments, the cyclodextrin is 2-hydroxypropyl-β-cyclodextrin, having an average molecular weight of about 1200 to about 1400 Da, and an average degree of substitution of about 0.5 to about 1.0 hydroxypropyl groups per glucopyranose unit. In some embodiments, the cyclodextrin is 2-hydroxypropyl-β-cyclodextrin, having an average molecular weight of about 1396 Da and an average degree of substitution of about 0.67 hydroxypropyl groups per glucopyranose unit.

This disclosure provides various embodiments of the dosage amount of the cyclodextrin. In some embodiments, the cyclodextrin may be administered in an amount ranging from 1000-40,000 mg/kg. This range includes all values and subranges therebetween, including 1000, 1200, 1400, 1600, 1800, 2000, 2100, 2200, 2300, 2400, 2500, 2600, 2700, 2800, 2900, 3000, 3500, 4000, 5000, 6000, 7000, 8000, 9000, 10,000, 20,000, 30,000, 40,000 mg/kg, or any combination thereof. In some embodiments, the dosage amount is based on a 2000 mg/kg murine dose, and may be scaled for human treatment, as is known in the art.

In some embodiments, the amount of cyclodextrin, such as 2-hydroxypropyl-β-cyclodextrin (HPBCD), is greater than about 13% w/w of the composition. In some embodiments, the amount of cyclodextrin, such as HPBCD, is about 20% w/w or greater of the composition. In other embodiments, the amount of cyclodextrin, such as HPBCD, is about 20% w/w to about 45% w/w of the composition. In some embodiments, the amount of HPBCD in the composition is about 30-45% w/w, or about 40% w/w of the composition. Applicant has found that less than 12.5% w/w cyclodextrin in a composition is ineffective in stimulating neurogenesis as described herein.

In some embodiments, it may be desirable to use derivatives of cyclodextrin, e.g., the so-called polyrotaxanes in place of or in addition to the cyclodextrins in the composition. Polyrotaxanes are a class of supramolecular materials in which β-cyclodextrins are threaded along a polymer chain capped with bulky terminal moieties. Examples of polyrotaxanes include 2-hydroxypropyl-β-cyclodextrin/plurionic-based polyrotaxanes, biocleavable plurionic/β-cyclodextrin polyrotaxanes, and the like.

In some embodiments, polyethylene glycol (PEG) is used, and the average molecular weight may range from 100 to 6000 Da. This range includes all values and subranges therebetween, including 100, 200, 300, 400, 500, 600, 700, 800, 900, 1000, 1200, 1400, 1600, 1800, 2000, 2100, 2200, 2300, 2400, 2500, 2600, 2700, 2800, 2900, 3000, 3500, 4000, 5000, 6000 Da, or any combination thereof. In some embodiments, polyethylene glycol having an average molecular weight of 100-1000 Da is used. In some embodiments, polyethylene glycol having an average molecular weight of 200-600 is used. In some embodiments, polyethylene glycol having an average molecular weight of 400 is used (i.e., PEG-400).

Mixtures of PEGs having different molecular weights are possible. In some embodiments, the amount of PEG may suitably range from 8.5 to 80% (w/w) of the composition by weight. This range includes all values and subranges therebetween, including 8.5, 9, 10, 15, 20, 25, 30, 35, 40, 45, 50, 55, 60, 65, 70, 75, 80%, or any combination thereof, based on the weight of the composition. In some embodiments, the PEG comprises greater than 8% w/w of the composition. In some embodiments, the PEG comprises about 20% to about 50% w/w, or about 40% to about 50% w/w, or about 45% w/w of the composition. Applicant has found that compositions having 8% or less of PEG in a composition is ineffective in stimulating neurogenesis as described herein.

In some embodiments, a composition for use in stimulating neurogenesis comprises, consists essentially of, or consists of 2-hydroxypropyl-β-cyclodextrin in an amount greater than 13% w/w and PEG-400 in an amount greater than 8% w/w of the composition.

In another embodiment, a composition for use in stimulating neurogenesis comprises, consists essentially of, or consists of 2-hydroxypropyl-β-cyclodextrin in an amount of about 20% w/w to about 40% w/w and PEG-400 in an amount of about 20% w/w to about 45% w/w of the composition.

In another embodiment, a composition for use in stimulating neurogenesis comprises, consists essentially of, or consists of 2-hydroxypropyl-β-cyclodextrin in an amount of about 20% w/w and PEG-400 in an amount about 45% w/w of the composition.

In still another embodiment, a composition for use in stimulating neurogenesis comprises, consists essentially of, or consists of 2-hydroxypropyl-β-cyclodextrin in an amount of 15% to 25% w/w and PEG-400 in an amount of 40% to 50% w/w of the composition.

In some embodiments, a pharmaceutically acceptable carrier is present. In various embodiments, the pharmaceutically acceptable carrier is an organic solvent or oil. In certain embodiments, the pharmaceutically acceptable carrier is an organic solvent that enhances the penetration of an agent in the composition across a biological membrane such as the skin, blood-brain barrier, or a cell plasma membrane as discussed, for example, in *Percutaneous Penetration Enhancers*, by E. W. Smith and H. I. Maibach, CRC Press, Inc., Boca Raton, Florida, 1995. In certain embodiments, a penetration enhancer includes, but is not limited to, a sulfoxide such as dimethyl sulfoxide (DMSO) or decylmethylsulfoxide, alkanols such as ethanol, propanol, butanol, hexanol, octanol, nonanol, decanol, and 2-butanol, fatty alcohols such as caprylic, decyl, lauryl, myristyl stearyl, and linolenyl alcohol, aliphatic fatty acid esters such as isopropyl n-butyrate, and isopropyl n-hexanoate, alkyl fatty acid esters such as ethyl acetate, methyl acetate, butyl acetate, and methylpropionate, polyols such as glycols, and polyethylene glycol, amides such as dimethylacetamide, dimethylformamide, pyrrolidone and pyrrolidone derivatives, cyclic amides, diethanolamine, and triethanolamine, anionic surfactants such as sodium laurel sulfate and sodium laurate, cationic surfactants such as benzalkonium chloride, cetylpyridinium chloride, and cetyltrimethyl ammonium bromide, non-ionic surfactants such as poloxmer 231, poloxmer 182, BRIJ 30, BRIJ 93, BRIJ 96, TWEEN 20, and TWEEN 80, terpenes such as limonene, carene, pinene, terpinol, carvone, methone, and terpene oxides, alkanones such as n-heptane, n-tetradecane, and organic acids such as salicylic acid, citric acid, and succinic acid.

In some embodiments, the pharmaceutically acceptable carrier is DMSO, petrolatum, mineral oil, castor oil, corn oil, glycerol, tocopherol, dimethyl formamide, dihydrolevoglucosenone (i.e., CYRENE), γ-butyrolactone (GBL), N-methyl-2-pyrrolidone (NMP), dimethylacetamide (DMAc), ethanol, or a combination thereof. In some other embodiments, the composition comprises a commercially available excipient or carrier, for example, to formulate the composition as a parenteral formulation, such as an intramuscular formulation, a subcutaneous formulation, an intravenous formulation, or the like.

In some embodiments, the pharmaceutically acceptable carrier is DMSO, dimethyl formamide (DMF), dihydrolevoglucosenone (i.e., CYRENE), γ-butyrolactone (GBL), N-methyl-2-pyrrolidone (NMP), dimethylacetamide (DMAc), ethanol, or a combination thereof.

While certain examples described herein employ DMSO as a pharmaceutically acceptable carrier, similar results can be attained using other carriers disclosed herein, for example, a carrier recited in one of the preceding paragraphs.

In other embodiments, the pharmaceutically acceptable carrier is a buffer or one or more buffering agent such as phosphate buffered saline, saline, saline-sodium citrate, tris-acetate-EDTA, tris-borate-EDTA, tris-EDTA, phosphoric acid, citric acid, acetic acid, histidine, lactic acid, tromethamine, gluconic acid, aspartic acid, tartaric acid, succinic acid, malic acid, fumaric acid, sodium acetate, sodium phosphate, sodium citrate, potassium acetate, potassium phosphate, potassium citrate, and the like. The concentration of a buffer to be added to the composition can be between about 20 and 100 mM, such as between about 25 mM and 100 mM, or about 25 to 50 mM, about 25 mM to 75 mM, or about 50 to 70 mM, in an aqueous solution but is not limited thereto.

In some embodiments, a method of stimulating neurogenesis comprises administering to a subject a composition comprising 2-hydroxypropyl-β-cyclodextrin (HPBCD), PEG-400, and a pharmaceutically acceptable carrier.

In other embodiments, a method of stimulating neurogenesis comprises administering to a subject a composition consisting essentially of 2-hydroxypropyl-β-cyclodextrin (HPBCD) and PEG-400. In other embodiments, a method of stimulating neurogenesis comprises administering to a subject a composition consisting essentially of 2-hydroxypropyl-β-cyclodextrin (HPBCD), PEG-400, and a pharmaceutically acceptable carrier. In still other embodiments, a method of stimulating neurogenesis comprises administering to a subject a composition consisting of 2-hydroxypropyl-β-cyclodextrin (HPBCD), PEG-400, and a pharmaceutically acceptable carrier. Preferably, the HPBCD is present in an amount of about 13% to about 45% w/w and the PEG-400 is present in an amount of greater than 8% w/w of the composition.

In other embodiments, a method of stimulating neurogenesis comprises administering to a subject a composition consisting of 2-hydroxypropyl-β-cyclodextrin (HPBCD) and PEG-400. In some embodiments, a method of stimulating neurogenesis comprises administering to a subject a composition consisting of 2-hydroxypropyl-β-cyclodextrin (HPBCD), PEG-400, and a pharmaceutically acceptable carrier, wherein the pharmaceutically acceptable carrier is selected from the group consisting of DMSO, dimethyl formamide DMF), dihydrolevoglucosenone (i.e., CYRENE), γ-Butyrolactone (GBL), N-Methyl-2-pyrrolidone (NMP), Dimethylacetamide (DMAc), ethanol, and a combination thereof. Preferably, the HPBCD is present in an amount of about 13% to about 45% w/w and the PEG-400 is present in an amount of greater than 8% w/w of the composition.

In various embodiments, the relative amount of cyclodextrin to PEG can be about 3 grams to about 5 grams of cyclodextrin; and about 8 milliliters to about 10 milliliters of PEG (e.g., a ratio of about 5:8 (g:mL) to about 3:10 (g:mL)). In yet other embodiments, the relative amounts of cyclodextrin to PEG is about 4 grams of cyclodextrin wherein cyclodextrin is HPBCD; and about 9 milliliters of PEG wherein PEG is PEG-400. In further embodiments, HPBCD is dissolved in water to form a first solution, PEG-400 is dissolved in a carrier to form a second solution, and the first and second solution are optionally combined to form a third solution; wherein the ratio of HPBCD to water is about 4 grams of HPBCD to about 15 milliliters of water, and the ratio of PEG-400 to carrier is about 9 milliliters of PEG to about 1 milliliter of carrier.

In various embodiments, the first and second solution are combined to form a third solution, wherein the amount of the third solution administered to the subject is about 1 microliter per gram of body weight to about 100 microliters per gram of body weight (e.g., about 1 mL/kg (solution/body weight) to about 100 mL/kg (solution/body weight), about 2 mL/kg to about 50 mL/kg, about 3 mL/kg to about 30 mL/kg, about 4 mL/kg to about 20 mL/kg, about 5 mL/kg to about 15 mL/kg, about 8 mL/kg to about 12 mL/kg, or about 10 mL/kg). In certain embodiments, the amount of the third solution administered to the subject is about 10 microliters per gram of body weight.

In some embodiments, the cyclodextrin/PEG composition may be administered in a monthly dose amount of about 500 mg/kg to about 1500 mg/kg, or about 500 mg/kg to about 1000 mg/kg. In other embodiments, the cyclodextrin/PEG composition may be administered in a monthly dose amount of about 100 mg to about 750 mg. Administration regimens are described in, for example, U.S. Provisional Application No. 62/885,053, International Publication. No. WO 2020/092107 (Hrynkow), and its corresponding U.S. publication, which are incorporated herein by reference.

In additional embodiments, the subject in need of therapy for stimulation of neurogenesis suffers from tactile allodynia, a brain/neurodegenerative disorder, an immunological response disorder, or a combination thereof. In other embodiments, the neurodegenerative disorder is a memory disorder, cognition disorder, learning disorder, defects in hippocampal function, or a combination thereof. In yet other embodiments, the subject has an intellectual disability. In other embodiments, subject in need of neurogenesis suffers from a neurodegenerative disorder, brain injury, nerve injury, psychiatric disorders, or aging.

In some embodiments, the neurodegenerative disorder may be one of acute disseminated encephalomyelitis, amyotrophic lateral sclerosis (ALS), retinitis pigmentosa, mild cognitive impairment, senile dementia, progressive supranuclear palsy, subcortical dementias, Wilson disease, multiple infarct disease, arteriosclerotic dementia, AIDS associated dementia, cerebellar degeneration, spinocerebellar degeneration syndromes, Friedreich's ataxia, ataxia telangiectasia, epilepsy-related brain damage, spinal cord injury, restless legs syndrome, striatonigral degeneration, cerebral vasculitis, mitochondrial encephalomyopathies, neuronal ceroid lipofuscinosis, spinal muscular atrophies, lysosomal storage disorders with central nervous system involvement, leukodystrophies, urea cycle defect disorders, hepatic encephalopathies, renal encephalopathies, metabolic encephalopathies, porphyria, bacterial meningitis, viral meningitis, meningoencephalitis, prion diseases, poisonings with neurotoxic compounds, Guillain Barre syndrome, chronic inflammatory neuropathies, polymyositis, dermatomyositis, or radiation-induced brain damage. Other neurodegenerative disorders include Alpha-mannosidosis, Cystinosis, Danon disease, Fabry disease, Farber disease, Fucosidosis, Galactosialidosis, Gaucher disease (Type I, Type II, Type III), GM1 gangliosidosis (infantile, juvenile and adult), I-Cell disease (Mucolipidosis II), Infantile Free Sialic Acid Storage Disease, Juvenile Hexosaminidase A Deficiency, Krabbe disease (Infantile and late onset), Lysosomal acid lipase deficiency (early and late), Metachromatic Leukodystrophy, Pseudo-Hurler polydystrophy (Mucolipidosis IIIA), MPSI (Hurler Syndrome), MPS II (Hunter syndrome), Sanfilippo syndrome Type A (MPS III A), Sanfilippo syndrome Type B (MPS III B), Sanfilippo syndrome Type C (MPS III C), Sanfilippo syndrome Type D (MPS III D), Morquio Type A (MPS IVA), Morquio Type B (MPS IVB), MPS IX (Hyaluronidase Deficiency), MPS VI (Maroteaux-Lamy), MPS VII (Sly Syndrome), Mucolipidosis I (Sialidosis), Mucolipidosis IIIC, Mucolipidosis type IV, Multiple sulfatase deficiency, Niemann-Pick Disease, Type A, Niemann-Pick Disease, Type B, Niemann-Pick Disease, Type C, Neuronal Ceroid Lipofuscinoses, Pompe disease, Pycnodysostosis, Sandhoff disease (infantile, juvenile and adult), Schindler disease, Salla disease (Sialic Acid Storage Disease), Tay-Sachs disease, Wolman disease, chronic traumatic encephalopathy, Alzheimer's disease (AD), Parkinson disease (PD), Huntington disease (HD), Frontotemporal dementia (FTD-3 subtype), Charcot-Marie Tooth disease type 2B, Neuronal ceroid lipofuscinoses/Batten disease (NCL), Creutzfeldt-Jakob disease, Autosomal dominant Spastin hereditary spastic paraplegia (ADHSP), Chediak-Higashi syndrome (CHS), and Inclusion body myositis (IBM).

In some embodiments, the psychiatric disorder may include anxiety disorders including, but not limited to, acute stress disorder, panic disorder, agoraphobia, social phobia, obsessive-compulsive disorder, posttraumatic stress disorder, and generalized anxiety disorder; childhood disorders including, but not limited to, attention-deficit hyperactivity disorder, Asperger's disorder, autistic disorder, conduct disorder, oppositional defiant disorder, separation anxiety disorder, and Tourette's disorder; eating disorders including, but not limited to, anorexia nervosa, and bulimia nervosa; mood disorders including, but not limited to, major depressive disorder, bipolar disorder (manic depression), cyclothymic disorder, and dysthymic disorder; cognitive disorders including, but not limited to, delirium, multi-infarct dementia, dementia associated with alcoholism, dementia of the Alzheimer type, and dementia; personality disorders including, but not limited to, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder, and obsessive-compulsive personality disorder; psychotic disorders including, but not limited to, schizophrenia, delusional disorder, brief psychotic disorder, schizophreniform disorder, schizoaffective disorder, and shared psychotic disorder; substance-related disorders including, but not limited to, alcohol dependence, amphetamine dependence, cannabis dependence, cocaine dependence, hallucinogen dependence, inhalant dependence, nicotine dependence, opioid dependence, phencyclidine dependence, and sedative dependence.

In some embodiments, the disclosure provides for methods of treating Kabuki syndrome. For example, one embodiment of method of treating an intellectual disability of Kabuki syndrome in a subject in need thereof comprising, consisting essentially of, or consisting of: administering to the subject in need of therapy for the syndrome a therapeutically effective amount of a composition comprising, consisting essentially of, or consisting of: a cyclodextrin and a polyethylene glycol (PEG), thereby treating intellectual disability in Kabuki syndrome.

In some embodiments, methods of treating an intellectual disability of Kabuki syndrome in a subject in need thereof comprises administering to the subject in need of therapy for the syndrome a therapeutically effective amount of a composition comprising, consisting essentially of, or consisting of a cyclodextrin, a polyethylene glycol (PEG), and a pharmaceutically acceptable carrier, thereby treating intellectual disability in Kabuki syndrome.

In some embodiments, methods of treating an intellectual disability of Kabuki syndrome in a subject in need thereof comprises administering to the subject in need of therapy for the syndrome a therapeutically effective amount of a composition comprising, consisting essentially of, or consisting of 2-hydroxypropyl-β-cyclodextrin and PEG-400, thereby treating intellectual disability in Kabuki syndrome.

In some embodiments, methods of treating an intellectual disability of Kabuki syndrome in a subject in need thereof comprises administering to the subject in need of therapy for the syndrome a therapeutically effective amount of a composition comprising, consisting essentially of, or consisting of 2-hydroxypropyl-β-cyclodextrin, PEG-400, and a pharmaceutically acceptable carrier, thereby treating intellectual disability in Kabuki syndrome. In some embodiments, the method of treating an intellectual disability of Kabuki syndrome in a subject in need thereof comprises administering to the subject in need of therapy for the syndrome a therapeutically effective amount of a composition comprising, consisting essentially of, or consisting of about 13% to about 45% 2-hydroxypropyl-β-cyclodextrin and greater than 8% w/w PEG-400, or in other embodiments, the composition comprises, consists essentially of, or consists of about 40% w/w 2-hydroxypropyl-β-cyclodextrin and about 45% w/w PEG-400.

In various embodiments, the disclosed composition is used for stimulating hippocampal neurogenesis, growing granule cell neurons, or a combination thereof. In other embodiments, methods for improving memory, learning and cognition in subjects having a neural or brain disease comprise administering a disclosed composition. In other embodiments, a method of stimulating hippocampal neurogenesis or growing granule cell neurons comprises administering a disclosed composition to a brain or a patient in need thereof.

In other embodiments, a composition as disclose herein may be used to stimulate neurogenesis in a healthy individual, or an individual showing no detectable brain abnormalities or conditions.

Figure 6:
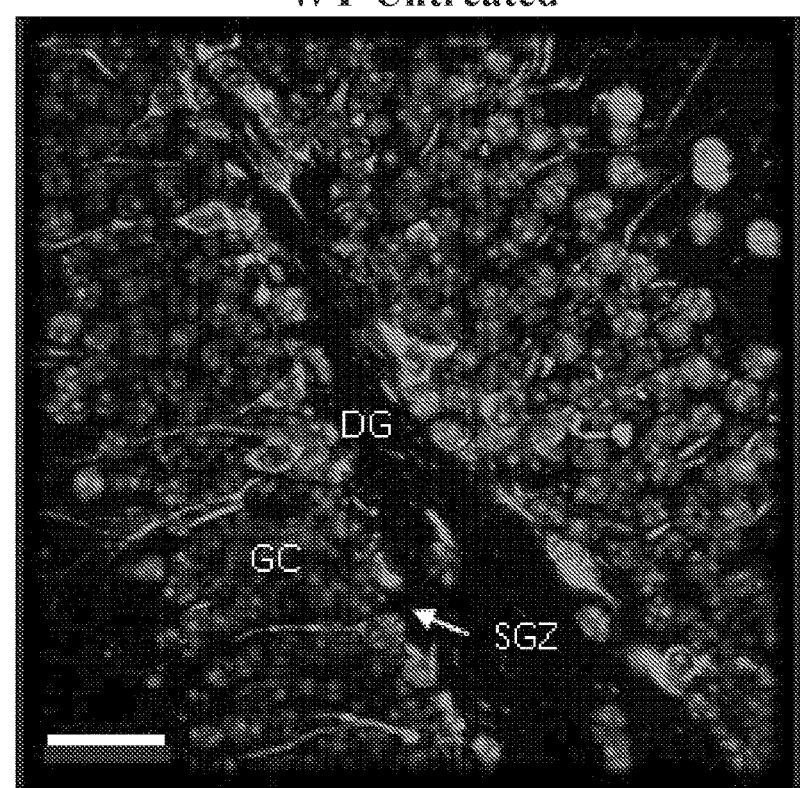
FIG. 6. Effects of drug-treatment on hippocampal neurogenesis in Kmt2d$^{+/bGeo}$ mice. Indirect immunofluorescence data in panels (a), (b), (c), (d) show reduced DCX positive cells in the sub granular zone of the hippocampus of Kmt2d$^{+/bGeo}$ (Kbk) mice. Kbk mice treated with drug (PEG+HPBCD+DMSO; Kbk−Drug) showed significant elevation in the DCX positive neurons compared to DMSO injected animals (Kbk−DMSO) via increased DAPI staining. Scale bar, 25 μm. Quantification of DCX positive neurons in the entire subgranular is zone is shown in the scatter plot (e). Data is from 4-6 mice per group. 4-6 sections/mouse were analyzed. Un, untreated. ****P<0.0001, ANOVA.
Figure 6:
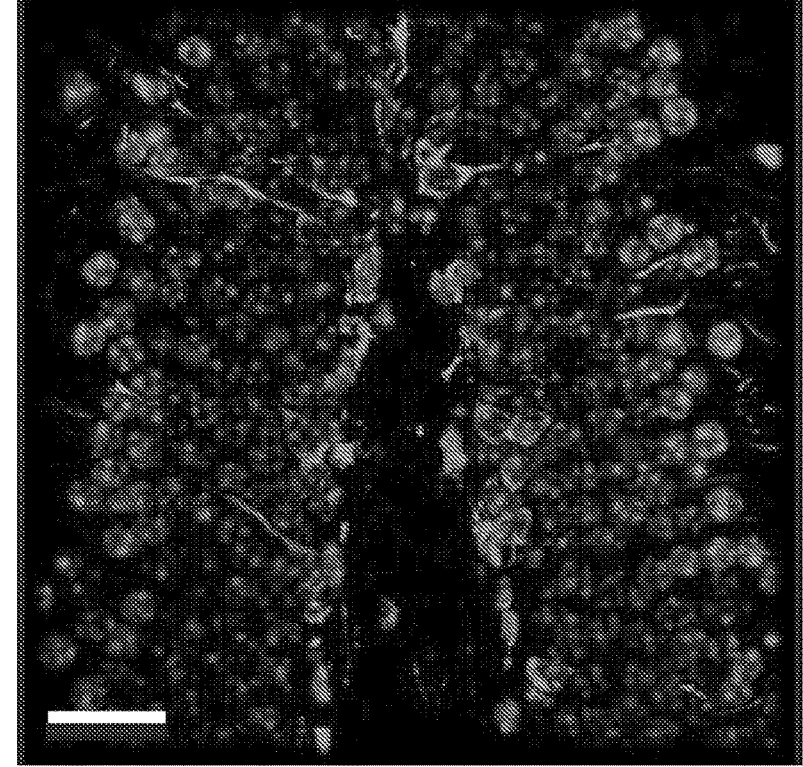
Figure 6:
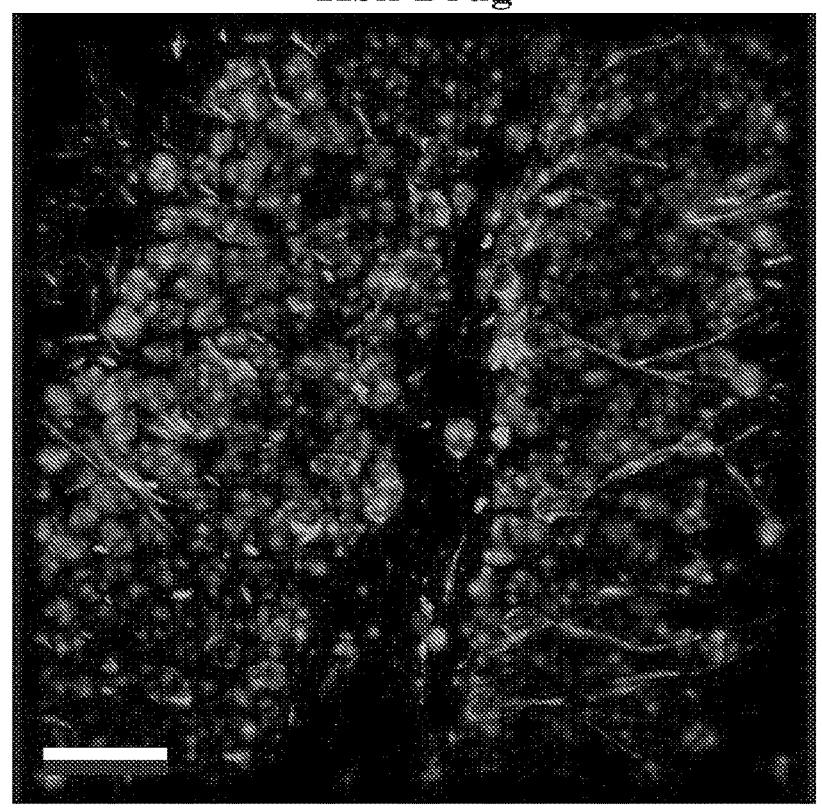
Figure 6:
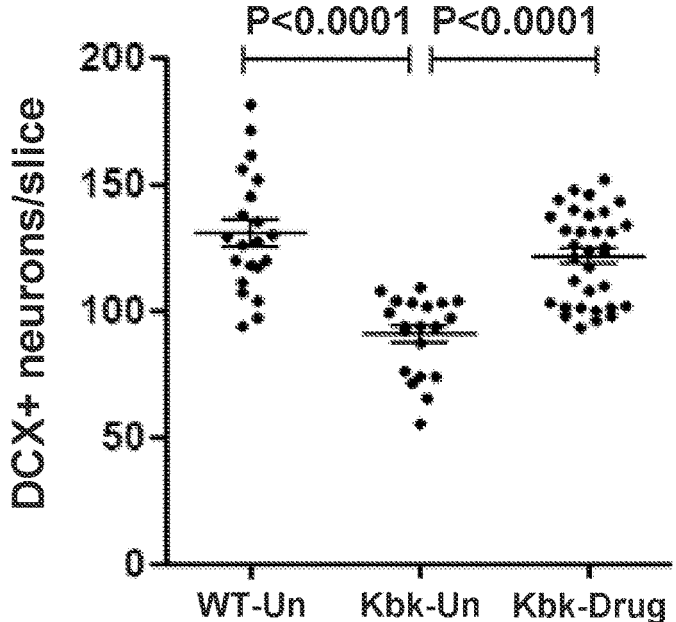

In some embodiments, the compositions and method used herein to cause or promote stimulation of neurogenesis in a subject may be characterized by certain biological events as compared to the same biological event in untreated subjects. For example, use of the compositions and methods disclosed herein may cause an increase in DCX-positive neurons per imaging slice of about 20%, about 25%, about 30%, about 35%, about 40%, about 45%, or about 50% in treated versus untreated subjects where the subjects have neurological disorder (see, for example, FIG. 6). Composition and methods of the disclosure also may cause an increase in in DCX-positive neurons of about 20%, about 25%, about 30%, about 35%, about 40%, about 45%, or about 50% in treated subjects compared to untreated subjects (where the subject has no known neurological disorder). This increase may be greater in male subjects as compared to female subjects. For example, male subjects may have an increase in DCX-positive neurons of about 50%, about 60%, about 70%, about 80%, about 90%, about 100%, about 110%, or about 120% in male subjects treated with the disclosed compositions compared to untreated male subjects (see, for example, FIG. 9).

Figure 8:
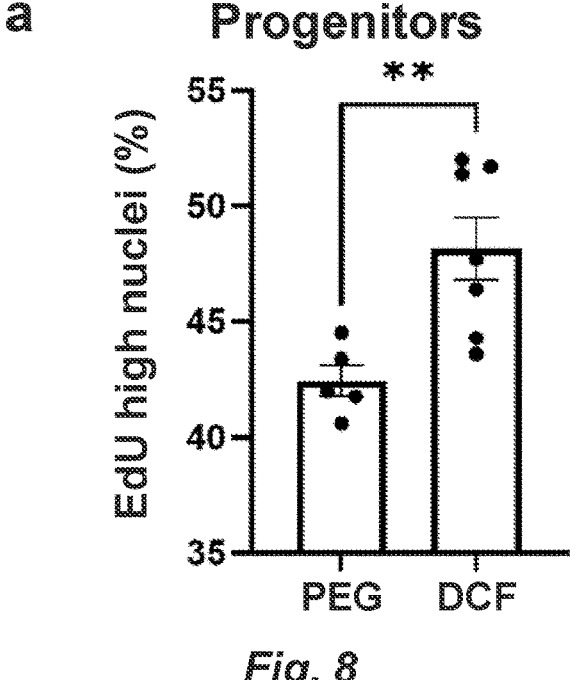
FIG. 8. Quantitative analysis of drug-induced EdU-positive nuclei in neural progenitors but not in glial cells in kbk mice using a double-combination formula (DCF). (a) percentage of progenitor cells having an EdU high nuclei percentage after treatment with PEG and DMSO, and DCF (HPBCD in PEG and DMSO). (b) Percentage of glial cells having an EdU low nuclei percentage after treatment with PEG and DMSO, and DCF (HPBCD in PEG and DMSO).
Figure 8:
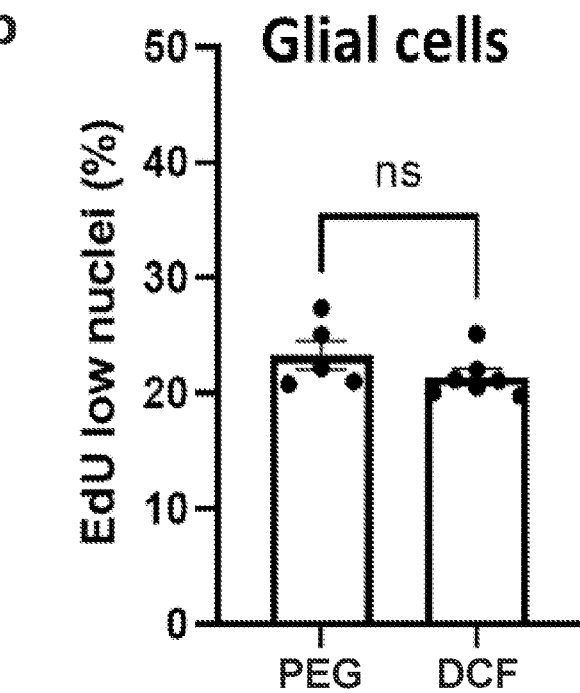
Figure 8:
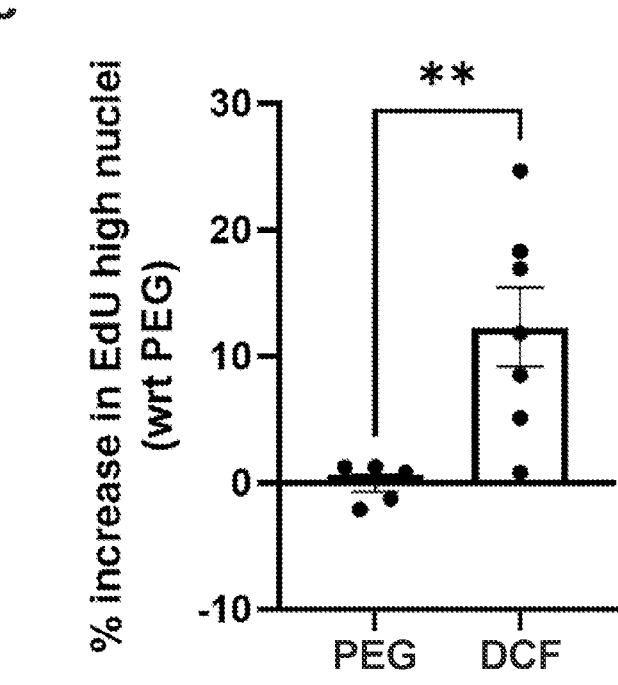

Subjects having a neurological disorder treated with Cyclodextrin/PEG combination had about a 5%, about a 10%, about a 15%, or about a 25% increase in EdU high nuclei in neural progenitor cells compared to untreated subjects having the neurological disorder (FIG. 8A, 8C).

Treatment with the DCF showed about a 1-fold increase, about a 1.5-fold increase, about a 2-fold increase, about a 2.5-fold increase, about a 3-fold increase, about a 3.5-fold increase, about a 4-fold, about a 4.5-fold increase, or about a 5-fold increase in neuronal biomarkers indicative of neurogenesis in treated subjects as compared to untreated subjects. For example, FIG. 10 shows a 3-fold to 4-fold increase in the marker Sox2 expression, a 1-fold to 2-fold increase in the marker Sox4 expression, a 1-fold to 3.5-fold increase in the marker Nestin expression, and a 1-fold to 2.5-fold increase in the marker DCX expression, in neural progenitor cells of DCF treated subjects compared to subjects treated only with PEG.

Use of the DCF on subjects also caused a significantly increase in the Discrimination Index (DI) values between treated and untreated subjects. For example, DCF treatment may cause about a 10-point increase, about a 15-point increase, about a 20-point increase, or about a 25 point or more increase in DI value compared to untreated subjects or subjects treated only with PEG or DMSO (where the subjects have a neurological disorder). The DI value increase may be higher in females as compared to males (see, for example, FIGS. 11-12).

In some embodiments, a method for stimulating neurogenesis in a subject comprises administering to the subject a therapeutically effective amount of a composition comprising a cyclodextrin and a polyethylene glycol, thereby stimulating the neurogenesis, the neurogenesis comprising of one or more of a 3-fold to about a 4-fold increase in Sox2 expression, about a 1-fold to about a 2-fold increase in Sox4 expression, about a 1-fold to about a 3.5-fold increase in Nestin expression, and about a 1-fold to about a 2.5-fold increase in DCX expression, in neural progenitor cells compared to subjects treated with only PEG as the active agent, and optionally DMSO.

This disclosure provides various embodiments of the timing of the administration. For example, administering may occur once or more than once. In some embodiments, the administering is carried out periodically or substantially periodically, for example, daily, weekly, monthly, a multiple thereof, a fraction thereof, or a combination thereof. In some embodiments, the administering is carried out daily, a multiple thereof, a fraction thereof, or a combination thereof. In some embodiments, the administering is carried out weekly, a multiple thereof, a fraction thereof, or a combination thereof. In some embodiments, the administration may occur regularly, e.g., every week throughout the duration of treatment, or it may occur irregularly, e.g., once a week for a few weeks, then twice a week or not at all for a few weeks, etc. Similarly, in some embodiments, a rest period of non-administration may occur between administrations. The rest period may occur regularly or irregularly.

In some embodiments, the composition is administered parenterally. In further embodiments, parenteral administration is intramuscular (IM), subcutaneous (SC), intravenous (IV), or intrathecal. In other embodiments, routes of administration may, for example, include rectal, transmucosal, buccal, intravaginal, or intestinal administration; direct intraventricular, intravenous, intraperitoneal, intranasal, or intraocular injections, and optionally in a depot or sustained release formulation. Furthermore, one may administer the composition in a targeted drug delivery system, for example in a liposome.

In some embodiments, a cyclodextrin/PEG composition may be administered directly to the central nervous system (CNS) of a subject. Preferably, direct delivery to the CNS is via intrathecally or intracerebroventricularly administration.

The cyclodextrin/PEG compositions may be administered with one or more additional therapeutic agents such as, but not limited to, ABBV-8E12 (anti-tau antibody), AC-1204 (glucose stimulant), ACI-24 (anti-Abeta vaccine), ACI-35 (anti-pTau vaccine), aducanumab (BIIB037) (amyloid beta mAb), AGB101(levetiracetam low-dose), ALZ-801 (amyloid beta-protein inhibitor), ALZT-OP1 (amyloid beta-protein inhibitor/inflammation mediator inhibitor), AMG520/CNP520 (BACE1 protein inhibitor), ANAVEX™ 2-73 (MI muscarinic receptor agonist/intracellular sigma 1 receptor agonist), AstraStem (mesenchymal stem cell therapy, AUS-131 (nonhormonal estrogen receptor agonist), AVN-101 (serotonin 6 receptor antagonist), AVN-322 (serotonin 6 receptor antagonist), A VP-786 (dextromethorphan analogue/ultra-low dose quinidine), AXS-05 (bupropion/dex-tromethorphan), azeliragon (TTP488) (RAGE antagonist), BAN2401 (anti-amyloid beta mAb), Bexarotene (RXR-selective retinoid analogue), BI 409306 (PDE9A inhibitor), BIIB076 (anti-tau antibody), BPB092 (anti-extracellular tau antibody), BNC375 (positive allosteric modulator), BPN14770 (type 4 cyclic nucleotide phosphodiesterase inhibitor), bryostatin 1 (protein kinase C stimulant), CAD 106 (amilomotide) (VLP immunotherapy vaccine), Corplex Donepezil (donepezil transdermal patch, Corplex Memantine (memantine transdermal patch, CPC-201 (donepezil/solifenacin combination), CPC-212 (next-generation acetyl-cholinesterase inhibitor), CPC-250 (next-generation acetylcholine-sterase inhibitor), Crenezumab (anti-amyloid beta antibody), CSP-1103 (amyloid beta-protein inhibitor), CSTC1 (BAC), CT1812 (amyloid beta oligomer receptor antagonist), E2027 (PDE9 inhibitor), E2609 (BACE1 protein inhibitor), EVT302 (MAO-B inhibitor), gantenerumab (amyloid beta-protein inhibitor), GCO21109 (purinoceptor P2Y6 agonist), HSRx-888 (donepezil/food-based compound), immune globulin/albumin, INP-102 intranasal, intepirdine (RVT-101) (serotonin 6 receptor antagonist), IONIS-M APTRx (tau-targeting protein), JNJ-54861911 (BACE inhibitor), JOT 106 (oral capsule of trans-res veratral), KPAX002-2 (proprietary version of methylphenidate), lanabecestat (BACE inhibitor), LM11A-31 (p75 neutrophin receptor), LMTX (tau protein aggregation inhibitor/TDP-43 aggregation inhibitor), LY3002813 (N3pG-amyloid beta antibody), LY3202626 (BACE inhibitor), LY3303560 (tau antibody), MI agonist (selective MI receptor agonist), MEDI1814 (anti-amyloid beta 42 mAb), mesenchymal stem cell therapy, MP-101(mGluR2/mGluR3 agonist), MSDC- 0160 (mTOT modulator), NB XT-00 1+Nobilis™ inhalation device (NMD A receptor antagonist), neflamapimod (VX-745) (p38 mitogen-activated protein kinase inhibitor), NGP 555 (gamma secretase complex modulator), nilvadipine soluble amyloid reducing/clearing agent), NPT088 (GAIM Ig fusion targeting amyloid-b, tau, a-synuclein), Nuplazid® pimavanserin, PF-05251749 (casein kinase 1 delta/epsilon), PF-06648671 (gamma secretase complex modulator), PF-06751979 (enzyme inhibitor), pioglitazone (low-dose) (PPARy agonist), piromelatine (melatonin agonist), Posi-phen® R-phenserine, Rexulti® brexpiprazole, RG6100 (tau protein inhibitor), RVT-103+RVT-104 (QAAM+cholinest-erase inhibitor), SAR228810 (anti-protofibrillar AB mAb), selective BACE 1 inhibitor, solanezumab (amyloid beta protein inhibitor), SUVN-502 (serotonin 6 receptor antagonist), SUVN-D4010 (serotonin 4 receptor agonist), SUVN-G3031 (histamine H3 receptor antagonist), T-817MA (amyloid beta-protein inhibitor), T3D-959 (PPAR-delta/gamma agonist), TAK-071 (muscarinic M 1 receptor modulator), TPI 287 (next-generation taxane), UB-311 (anti-amyloid endobody vaccine), UE-2343 (11b-HSD1 inhibitor), verubecestat (MK-8931) (BACE1 protein inhibitor), or combinations thereof.

Pharmaceutical Formulations

The compounds of the formulas described herein can be formulated as pharmaceutical compositions and administered to a mammalian host, such as a human patient, in a variety of forms. The forms can be specifically adapted to a chosen route of administration, e.g., parenteral administration, by intravenous, intramuscular, or subcutaneous routes.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

Useful dosages of the compositions described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The composition is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The composition can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Methods

One example of the double formulation has following components in the composition for the stimulation of neurogenesis:

1. HPBCD—2 hydroxypropyl β-cyclodextrin (Sigma Aldrich Cat #H107-100G);
2. PEG—Polyethylene glycol (Sigma Aldrich Cat #400 202398-500G); and optionally
3. a pharmaceutically acceptable carrier (e.g., DMSO, DMF, etc.)

Methodology for the preparation and administration of the double formulation (20 mL):

1. Take 1 mL carrier (e.g., DMSO) and add 9 mL PEG 400 and mix by gentle rocking for 10-15 min at RT.
2. Weigh 4 g of HPBCD and add 5 mL MilliQ water in 50 mL tube and vortex until HPBCD goes in solution. Make up the volume to 10 mL with MilliQ water.

3. Pour the HPBCD solution over the PEG+carrier solution (thus making total volume of 20 mL in 50 mL tube) and mix by gentle rocking for 10-15 min at room temperature (20-22° C.).
4. Make aliquots (size as desired, usually 1 mL into 20 vials) and store at −80° C. for up to 3 months.
5. Inject subject through therapeutically acceptable route (e.g., intraperitoneal) (volume of injection, 10 µL/gm body weight).

In some embodiments, corn oil, dimethyl formamide, dihydrolevoglucosenone (i.e., CYRENE), γ-butyrolactone (GBL), N-methyl-2-pyrrolidone (NMP), dimethylacetamide (DMAc), ethanol, DMSO, or a combination thereof may be used as the carrier.

Preferably, the volume of injection of the composition detailed above for stimulation of neurogenesis may comprise a volume of injection of 0.001 µL/gm body weight, 0.01 µL/gm body weight, 0.1 µL/gm body weight, 1 µL/gm body weight, 2 µL/gm body weight, 3 µL/gm body weight, 4 µL/gm body weight, 5 µL/gm body weight, 6 µL/gm body weight, 7 µL/gm body weight, 8 µL/gm body weight, 9 µL/gm body weight, 10 µL/gm body weight, 11 µL/gm body weight, 12 µL/gm body weight, 13 µL/gm body weight, 14 µL/gm body weight, 15 µL/gm body weight, 16 µL/gm body weight, 17 µL/gm body weight, 18 µL/gm body weight, 19 µL/gm body weight, or 20 µL/gm body weight.

Animals. Breeding pair of kabuki mouse model Km2d$^{+/βGeo}$ (cataloged as Kmt2dGt(RRT024)Byg) were obtained from Bay Genomics, University of California. These mice carried a heterozygous mutation in Kmt2d gene and were on the mixed background of C57BL/6J and 129/SvEv. The Kmt2d$^{+/βGeo}$ mice were backcrossed with WT C57BL/6J mice in Haldar lab and strain purity (99-100%) confirmed by genetic analysis at Jackson labs. Breeding was performed in-house by pairing female wild type (WT) mice with male heterozygous mutant mice. The mouse Km2d sequence may be found, for example NCBI Reference Sequence NC_000081.7 and XM_017316684.2, and the human Km2d sequence may be found at NCBI Reference Sequence NC_000012.12 and XM_006719614.4.

Novel Object Recognition assay. The object recognition test is used to assess memory in mice. The assay was conducted on three consecutive days. On day 1, mice were individually placed into a plastic container with black walls of size 37×29×17 cm and allowed to explore the arena for 10 minutes. On day 2, two identical objects were placed in the center (kept at equidistance from the wall and each other) and the time interacting with each object was recorded over 10 minutes. On the third day, one object was removed and replaced by a novel object. Lego towers and T25 tissue culture flask filled with white gravel were used as objects. Mice were placed in the arena for ten minutes and timed for interaction with each object. The arena and objects were cleaned with 70% ethanol between each mouse to eliminate olfactory cues. The discrimination index was calculated by using a formula, TN−TF/TN+TF, where TN and TF are time spent exploring novel and familiar objects respectively.

Von Frey Assay. Tactile sensitivity was measured by studying paw withdrawal frequency (PWF) using a series of von Frey filaments with incremental filament thickness (39). The mice were placed into an acrylic box and habituated in a quiet room for an hour. Mechanical stimulus was applied perpendicular to the mid-plantar surface of hind paws for 2 seconds with force enough to bend the filament. Each paw was stimulated 5 times by each filament with an interval of 5 seconds between each measurement. Only rapid paw withdrawal or prolonged paw withdrawal combined with flinching or licking of the paw were recorded. 50% paw withdrawal threshold was calculated. Left and right hind paws of each mouse were assessed on three consecutive days and average withdrawal threshold of each paw was used to plot the data. Lower 50% threshold value suggests higher tactile sensitivity.

Immunofluorescence assay and microscopy. Brain hemisphere was immersion fixed in 10% neutral buffered formalin (~4% paraformaldehyde) for 20-22 h and paraffin-embedded. 5 μM thick sagittal sections spaced at 40 μm collected at 4-6 different depths were processed for DCX staining. After dewaxing and hydration, DCX antigen was retrieved by boiling the sections in acidic condition for 30 min followed by a 20-minute incubation at the room temperature as the sections cool off. After blocking in 2% goat serum, sections were incubated with anti-DCX antibody (Santa Cruz Biotechnology, sc-271390, 1:50) overnight at 4° C. FITC conjugated secondary IgG (MP Biomedicals) was used at 1:1000 dilution. Sections were mounted using Vectashield (Vector Laboratories) containing DAPI for staining nuclei and visualized by fluorescence microscopy. DCX labeled brain sections were visualized by Olympus IX inverted fluorescence microscope using 40× oil-immersion objective lens (NA1.35) and the number of DCX+ cells in the inner margin of entire SGZ was manually counted. Digital images of consecutive 20 optical sections of 0.2 μm thickness were collected by Photometrix cooled CCD camera (CH350/LCCD) driven by DeltaVision software from Applied Precision (Seattle, WA, USA). DeltaVision software (softWoRx) was used to deconvolve these images. Images presented are maximum intensity projection of all 20 optical sections. Images were analyzed using 'softWoRx' or 'ImageJ' software (NIH, MD, USA). Also see Alam et al., Sci Transl Med. 2016Feb. 17; 8(326):326ra23.

RNA extraction and quantitative PCR. Formalin fixed paraffin embedded brain and liver were sectioned (sagittal in the case of brain, 4-5 μm) and total RNA was isolated using RNeasy FFPE kit (Qiagen, Germantown, MD, USA) which included treatment with DNAse. Total RNA from frozen spleen was isolated using RNeasy Plus Universal kit from Qiagen. The quantity of RNA was determined using Nanodrop 2000 (Thermo Fisher Scientific, Waltham, MA, USA).

Quantitative PCR (qPCR) was performed using Power SYBR Green RNA-to-CT 1-Step Kit and an ABI Prism 7500Fast real-time PCR system (Applied Biosystems, Grand Island, USA). The reaction was set in 20 μl using 100 nM primers and 5-100 ng total RNA as a template in duplicate wells. The thermal cycling parameters were as follows: step 1, 48° C. for 30 min; step 2, 95° C. for 10 min; step 3, 95° C. for 15 sec; step 4, 60° C. for 15 sec. Step 3-4 was repeated for 40 cycles followed by melt curve analysis.

Statistical Test. Graphs were plotted in MS Excel or GraphPad Prism 8.4.3. For comparing two groups student's t-test or Mann-Whitney U test was performed. For comparing more than two groups, one-way ANOVA with Tukey's posthoc analysis (parametric) or Kruskal-Wallis test (nonparametric) was performed. All statistical tests were done with GraphPad Prism 8.4.3 and were two-tailed. Statistical test and P values are indicated in figure legends. P<0.05 was considered significant. *P<0.05, P<0.01, *P<0.001, ****P<0.0001.

Example 2. a New Treatment to Stimulate Hippocampal Neurogenesis and Growth of Granule Cell Neurons Linked to Intellectual Disability in KS There are no known treatments that stimulate long term, hippocampal post-natal neurogenesis and growth of granule cell neurons linked to hippocampal function. Treatment of defect in hippocampal neurogenesis and granule cell neurons linked to memory, cognition, tactile allodynia and over all intellectual disability.

Figure 1:
FIG. 1. Molecular and hippocampal memory and sensory defects in the Kmt2d$^{+/bGeo}$ mouse model of Kabuki Syndrome. (a) Schematic of Kmt2d genes in Kmt2d$^{+/bGeo}$ mouse model in mixed C57BL/6J and 129/SvEv background (obtained from Bay Genomics, Univ. California). In this model, SET domain from one copy of the Kmt2d gene coding region (exon 52) is replaced with the βGeo cassette; (b) qPCR analysis showing Kmt2d transcript levels (measured by detection of Exon 52) were reduced by ~50 in the brain of Kmt2d$^{+/bGeo}$ (Kbk) relative to WT (n=5M, 5F per group); (c) H3K4-me3 level was reduced by 50% in the brain of Kbk relative to WT; (d) In the novel object recognition test, WT and Kbk mice showed no difference in positional preference for identical objects in the habituation/training phase. In the test phase, Kbk mice did not differentiate the novel object from the familiar (identical) object and spent significantly less time with the novel object compared to WT mice. n=14 WT (8M, 6F); n=14 Kbk (8M and 6F); (e) Kbk mice show increased mechanical allodynia compared to WT, as demonstrated by reduced 50% paw withdrawal threshold in response to von Frey filaments in both (left and right) hind paws n=16WT (8M, 8F); n=14 Kbk (8M+6F). P values as shown, student's t-test.
Figure 1:
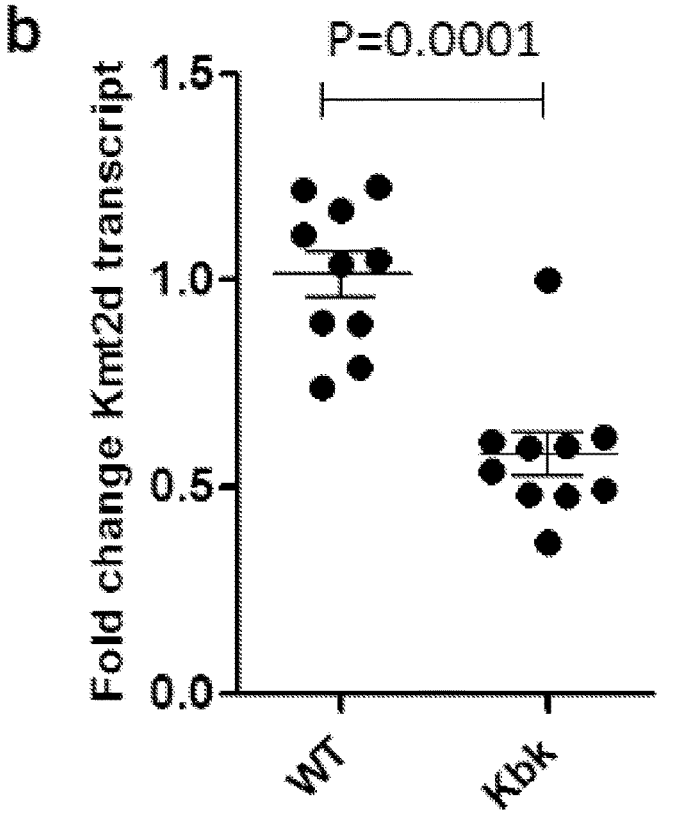
Figure 1:
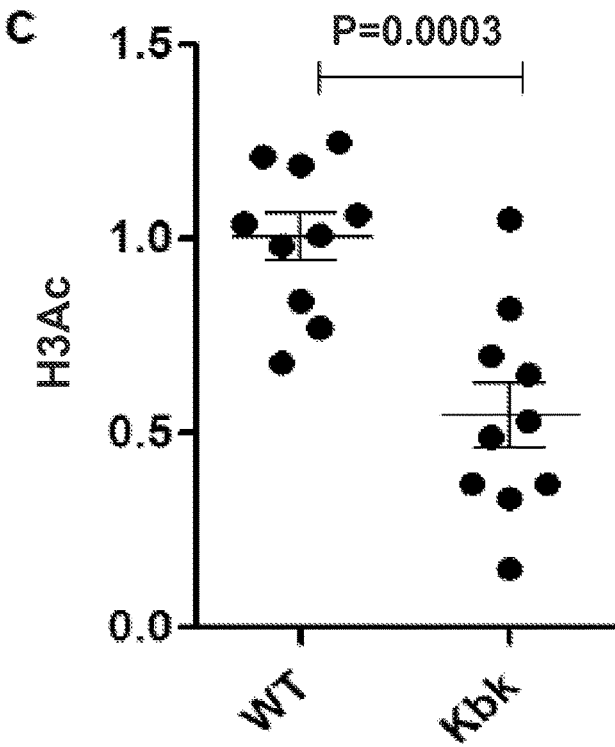
Figure 1:
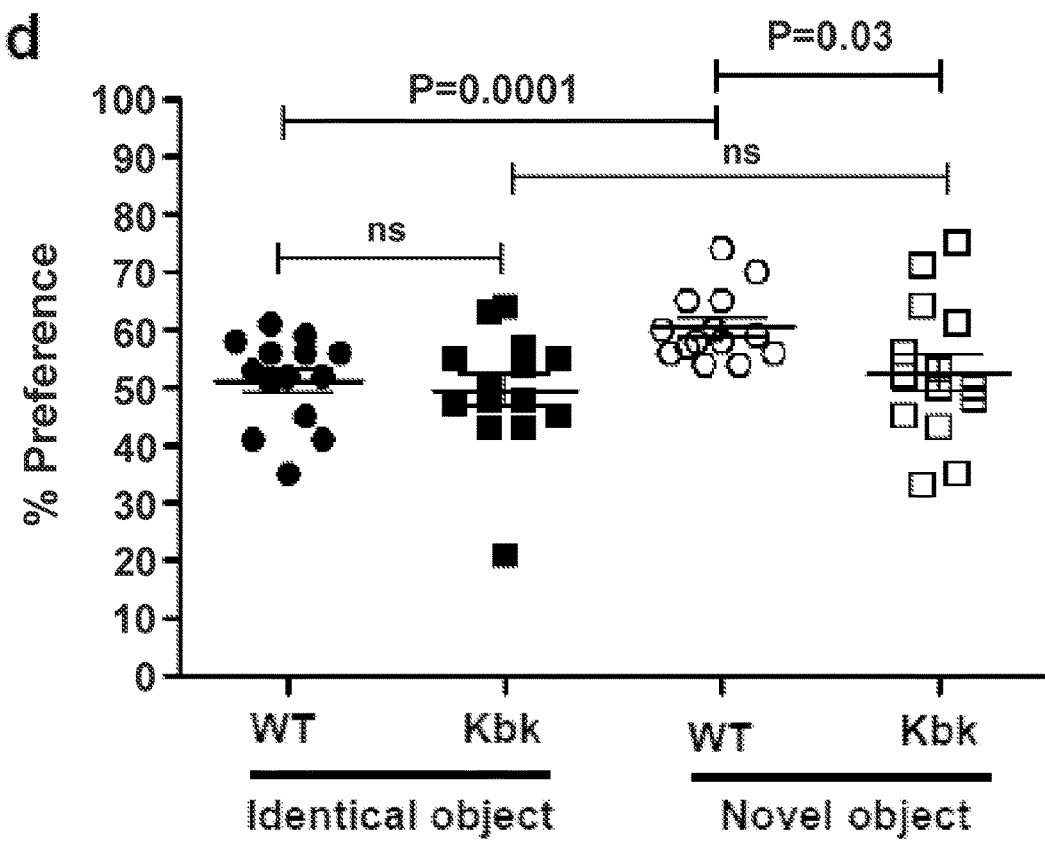
Figure 1:
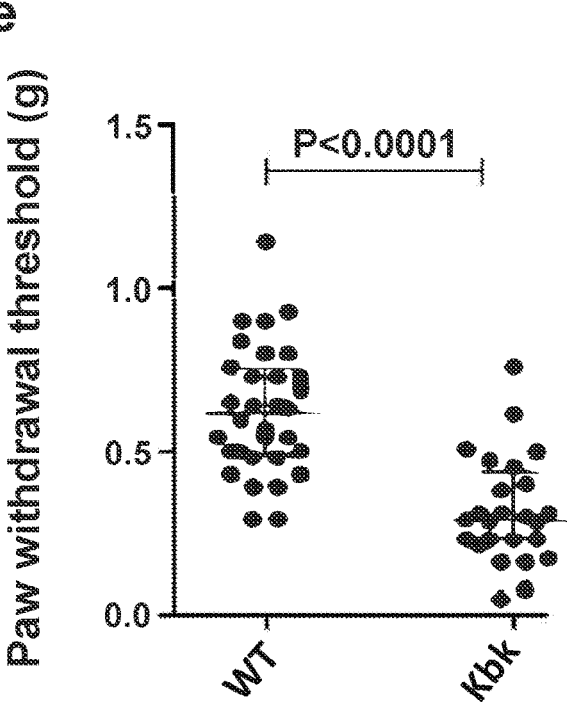
Figure 2:
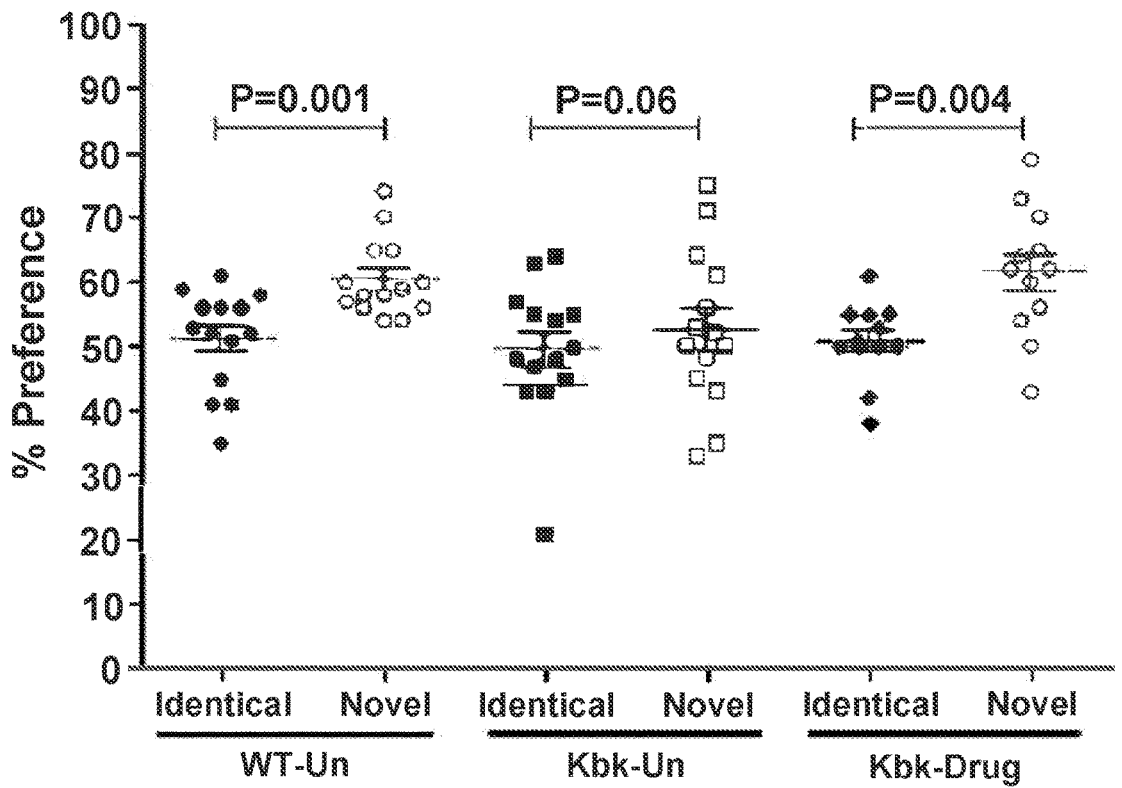
FIG. 2. Effects of drug-treatment on hippocampal deficit in the Kmt2d$^{+/bGeo}$ mice. WT and Kmt2d$^{+/bGeo}$ (Kbk) mice showed no difference in positional preference for identical objects in the habituation/training phase of the novel object recognition test. In the test phase, untreated Kbk Kbk (Kbk-Un) mice spent less time with a novel object relative to WT mice. n=16 WT (8 males, 8 females), n=12 Kbk (6M, 6F). Kbk mice treated with drug (PEG+HPBCD+DMSO; Kbk-Drug) showed no difference in preference for identical objects, relative to untreated Kbk (or WT) in the training phase. In the test phase, Kbk-Drug, mice spent more time with a novel object. P values as indicated, student's t-test.
Figure 3:
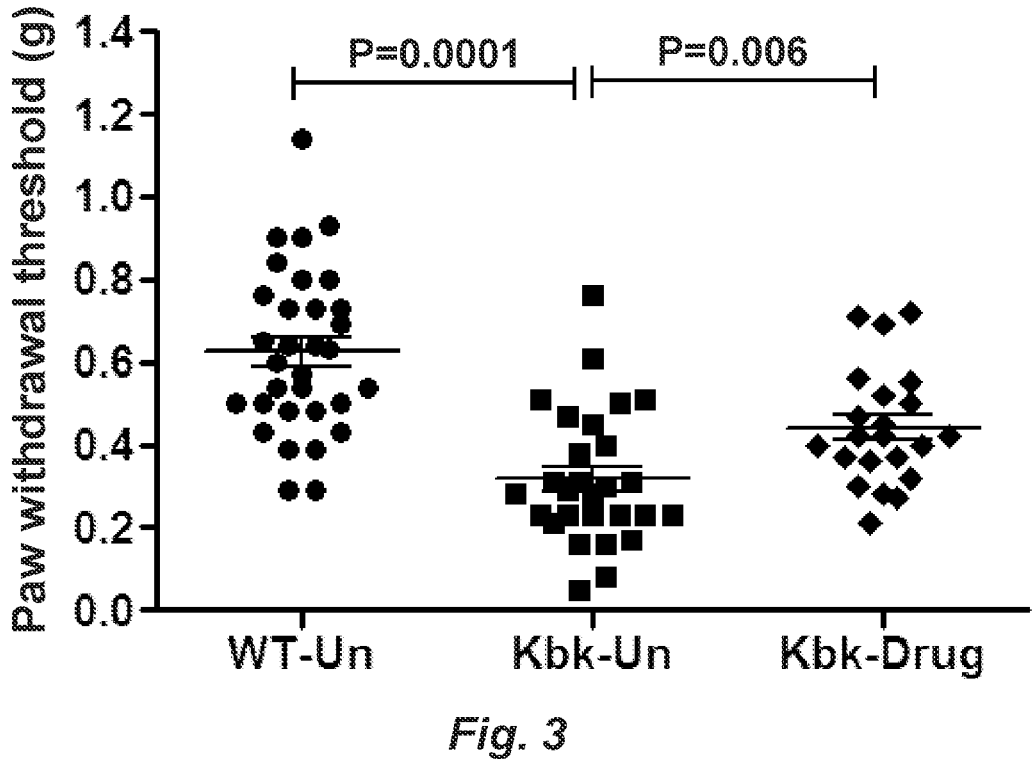
FIG. 3. Treatment with drug decreased mechanical allodynia in Kbk mice. Kbk mice show increased mechanical allodynia compared to WT, as demonstrated by reduced 50% paw withdrawal threshold in response to von Frey filaments in both (left and right) hind paws. Drug-treatment significantly reduced allodynia. n=16WT-Un (8M, 8F); n=14 Kbk-Un (8M+6F). n=11 Kbk-Drug (8M, 3F). P values as indicated, student's t-test.
Figure 4:
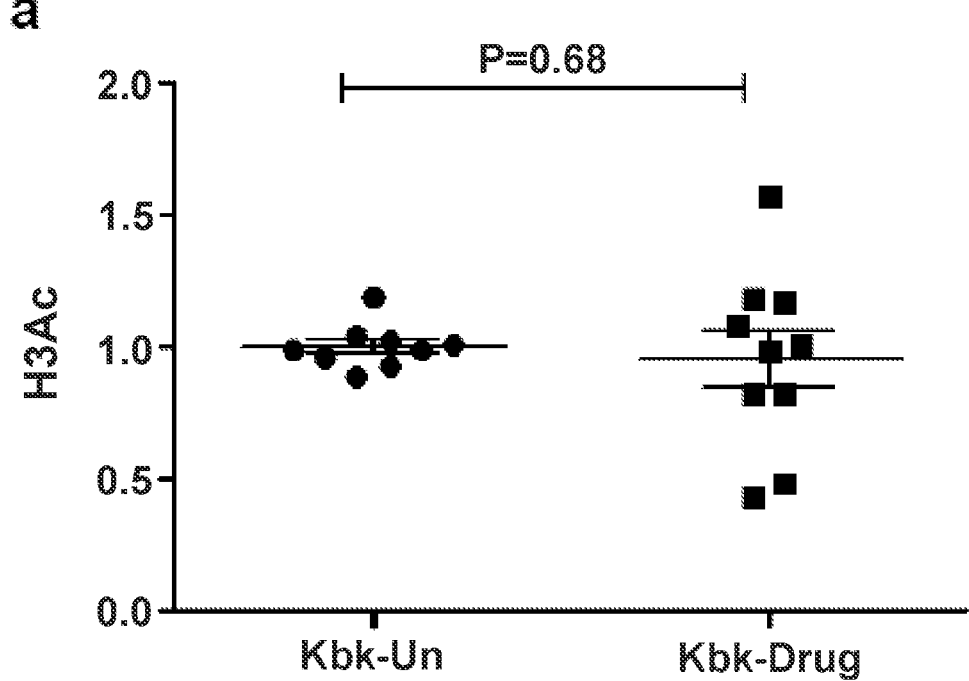
FIG. 4. HPBCD is required for improved hippocampal memory in Kmt2d$^{+/bGeo}$ mice and does not involve histone modification. (a) Novel object recognition assay showed kabuki mice treated with drug (HPBCD+PEG+DMSO) had higher discrimination index compared to DMSO+PEG (Kbk−DMSO+PEG) animals, suggesting HPBCD is essential for improving memory. Kbk−Un, n=27 (16M, 11F); DMSO+PEG, n=12 (6M+6F); Kbk−Drug, n=20 (9M+11F). **p<0.01, student's t test. (b-c) For analysis of histone modification, mice were injected with drug (HPBCD+PEG+DMSO) once weekly starting at 21-23 days of age, sacrificed at 90-100 days and brains were analyzed for (b) histone 3 lysine 4 trimethylation (H3K4-me3); and (c) histone 3 acetylation (H3Ac). n=9 (5F, 4M) for Kbk−Un and n=10 (5F and 5M). Treatment with drug had no significant changes in either of the histone modifications. All data were normalized for total histone protein. Kbk−Un (un-injected)Kmt2d$^{+/bGeo}$) were not untreated. The data points are relative to average of Kbk−un. P values as indicated, student's t test.
Figure 4:
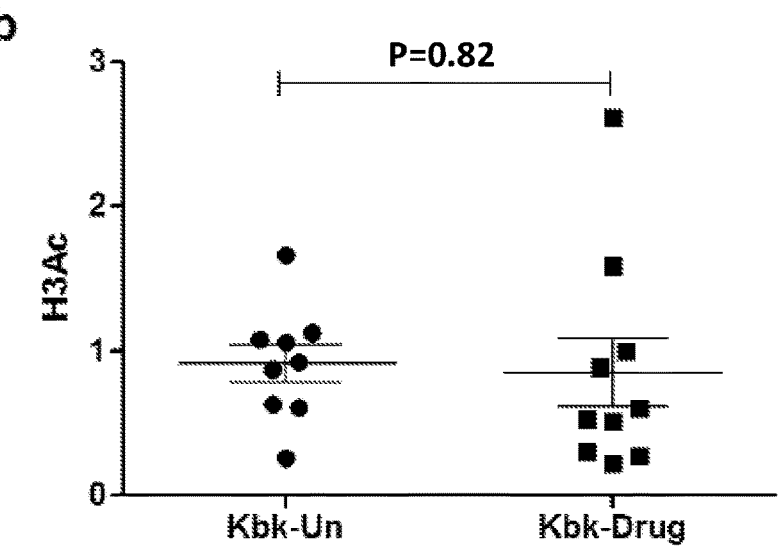

A mouse model of KS with heterozygous deletion of the enzymatically active (SET) domain in kmt2d yields a model with defects in hippocampal learning and memory (FIG. 1A-E). A treatment in development combines polyethylene glycol 400 (PEG) and hydroxypropyl-beta-cyclodextrin (HPβCD) and can be chronically administered in the KS mouse model to rescue correlates of hippocampal function learning and memory and tactile allodynia (FIG. 2 and FIG. 3). This treatment is not due to increase in histone acetylation or trimethylation in KS brain (FIG. 4A, FIG. 4B) and therefore occurs independent of the action of histone deacetylase inhibitors (HDACi).

Figure 5:
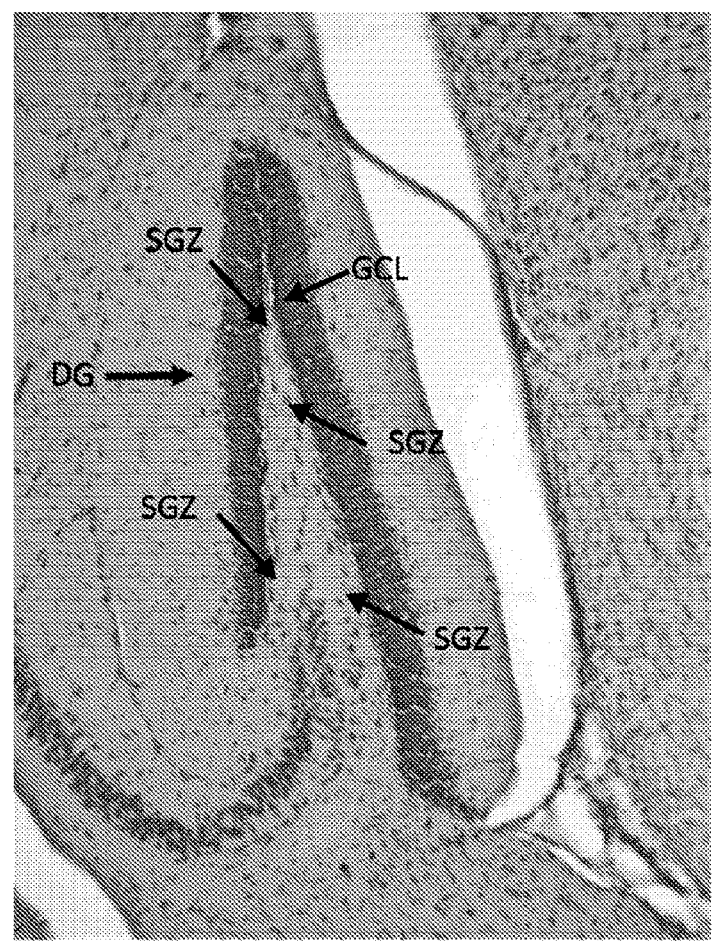
FIG. 5. Schematic of the dentate gyrus (DG) in mouse hippocampus. H&E-stained mouse brain section showing DG and sub granular zone (SGZ). SGZ resides at the inner side of the granule cell layer (GCL) and the site of post-natal hippocampal neurogenesis in DG, which is linked to memory, cognition and learning.
Figure 7:
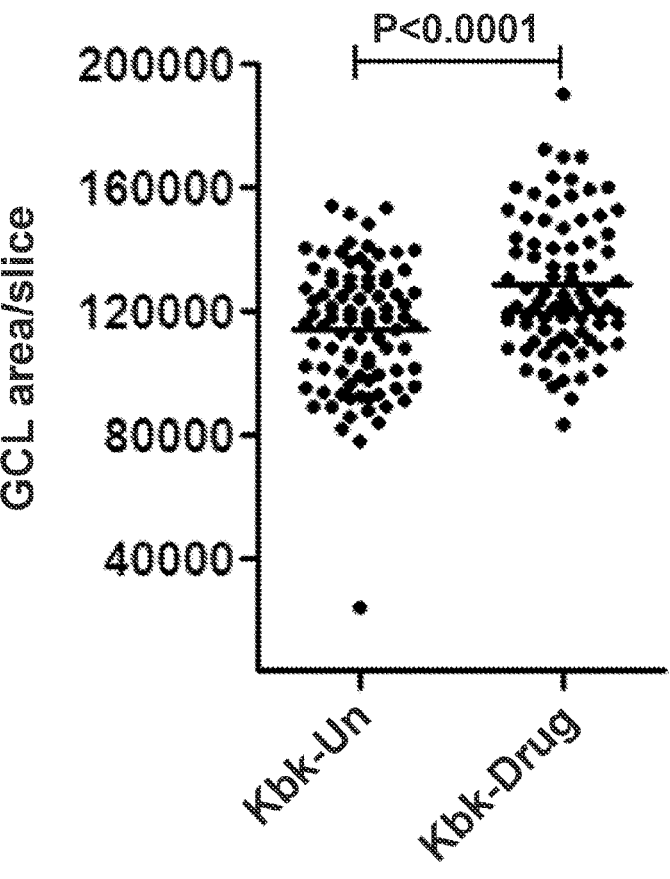
FIG. 7. Effects of drug-treatment on granule cell layer (GCL) of the dentate gyrus (DG) in brain of Kmt2d$^{+/bGeo}$ mice. Neural precursors from the SGZ mature into granule cell neurons that reside in the granule cell layer of the DG. Analysis of GCL area of untreated Kmt2d$^{+/bGeo}$ (Kbk−Un) mice as well as Kbk mice treated with drug (PEG+HPBCD+DMSO; Kbk−Drug). Data shown from 10 mice (5M+5F) per group. 7-10 sections/mouse were analyzed. Un, untreated. P values as indicated, student's t test. The finding show treatment with drug expand granule cells in the DG mice suggesting that neural precursors produced by post-natal neurogenesis in the SGZ mature to granule cells and contribute to hippocampal function.

Further, a mouse model of KS with heterozygous deletion of the enzymatically active (SET) domain in kmt2d yields a model with defects in hippocampal neurogenesis. FIG. 5 provides a schematic of dentate gyrus (DG) and its component parts. A treatment in development combines polyethylene glycol 400 (PEG) and hydroxypropyl-beta-cyclodextrin (HPβCD) and can be chronically administered in the KS mouse model to rescue correlates of hippocampal neurogenesis in the DG of the subgranular zone (SGZ; FIG. 6A-D). The KS also yields a model for reduced hippocampal granule cell neuron (see FIG. 5, for location of the granule cell layer (GCL) neurons). A treatment in development combines polyethylene glycol 400 (PEG) and hydroxypropyl-beta-cyclodextrin (HPβCD) and can be chronically administered in the KS mouse model to increase hippocampal granule cell layer (FIG. 7). This treatment does not increase in histone acetylation or trimethylation in KS brain (FIG. 4) and therefore stimulation of hippocampal post-natal neurogenesis and development of the granule cell layer, occurs independent of the action of histone deacetylase inhibitors (HDACi).

Example 3. a Therapy to Stimulate Post-Natal Neurogenesis and Granule Cell Neurons in the Hippocampus in Kabuki Syndrome Adult hippocampal neurogenesis generates granule cell neurons in the dentate gyrus (DG). The precursor cells, which give rise to adult neurogenesis reside in the subgranular zone (SGZ) of the DG. Stimulation of neurogenesis in the SGZ of the DG and increased granule cell neurons support hippocampal functions of learning and memory. A mouse model with impaired hippocampal function, decreased neurogenesis and reduced granule cells was used to develop a treatment that stimulates post-natal neurogenesis in the SGZ of the DG and increases hippocampal granule cell neurons. We disclose that this treatment improves hippocampal brain functions of cognition and memory in the mouse model with impaired hippocampi. We disclose that this treatment increases levels of neuroblasts, the stage of development immediately prior to mature granule cell neurons in the SGZ of the DG. And we now disclose it acts by stimulation of neural precursors in both impaired and normal hippocampi suggesting broad applicability in treatment of neurological disorders.

Kabuki syndrome (KS) is a multi-system disorder that compromises regulatory mechanisms underlying hypoxia. Varying degrees of intellectual disability appear to be associated with the majority of patients. KS is also associated with defects in as well as adult neurogenesis and reduced granule cells in the hippocampus (and loss of hippocampal functions of learning and memory). Since hippocampal neurogenesis and granule cell growth are needed for hippocampal functions of cognition, learning and memory, KS provides a monogenetic disorder to query post-natal hippocampal neurogenesis and development of granule cell neurons.

A mouse model of KS with heterozygous deletion of the enzymatically active (SET) domain in kmt2d yields a model with defects in hippocampal neurogenesis. It yields a model for reduced production of neural progenitor cells in the hippocampus. A treatment in development that combines polyethylene glycol 400 (PEG) and hydroxypropyl-beta-cyclodextrin (HPβCD) can be administered in the KS mouse model to stimulate proliferation of neural progenitor cells (marked with the dye EdU) isolated from the hippocampus, while PEG alone has no effect (FIG. 8A). The treatment does not induce proliferation of glial cells (FIG. 8B), indicating it is selective for the production of progenitors committed to neurogenesis. The treatment specifically stimulates 10-25% increase in neural progenitor cells, as shown in FIG. 8C.

The effect of this treatment was also investigated in mice lacking any known genetic defect (FIG. 9). Although hippocampal neurogenesis is an active process during embryonic and early development, it is known to decrease by the young adult stage (10-12 years of age) in humans, which corresponds to approximately 60-70 day of age in mice. As shown in FIG. 9, the drug promoted higher levels of neuroblast formation (marked by DCX) compared to control (FIG. 9B versus 9A) in the SGZ of the DG of the hippocampus in females and males (F, M, FIG. 9C). The data in FIG. 10 indicates that the drug (DCF) but not control (PEG) stimulates the production of neural progenitors (marked by Sox 2 and Sox 4), neuroblasts (DCX) and early neurons (Nestin) in the hippocampus of both male and female mice. Together the data in FIG. 9 and FIG. 10 support that the drug (DCF) stimulates a physiological process of neurogenesis in the hippocampus, independent of genetic defect and may be applicable to a wide range of neurologicalconditions where the pathway is not impaired.

Further, using the Novel Object Recognition (NOR) test, which is a well-established and widely used measure of learning and memory in mice, Kmt2d$^{+/\beta Geo}$ animals showed reliable memory and learning defects as measured by a significant reduction in the Differential Index (DI) compared to wild type mice in the NOR test (FIG. 11). DMSO, and DMSO+PEG had no significant effect. Unexpectedly, HPBCD+PEG+DMSO significantly increased the DI to levels seen in wild type mice (FIG. 11). In males, the P value=0.06 and in females P<0.05 (FIG. 12A, 12B). Together, these data suggested that memory improvement was dependent on HPBCD.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for treating Kabuki Syndrome in a subject suffering therefrom comprising:
    administering to the subject a therapeutically effective amount of a composition comprising a cyclodextrin present in an amount of about 13% to about 45% w/w and a polyethylene glycol (PEG) present in an amount of greater than 8% w/w, thereby treating the Kabuki Syndrome.

2. The method of claim 1 wherein the cyclodextrin is one or more of 2-hydroxypropyl-β-cyclodextrin, hydroxypropyl-β-cyclodextrin, dimethyl-β-cyclodextrin, hydroxypropyl-α-cyclodextrin, and hydroxypropyl-γ-cyclodextrin.

3. The method of claim 2 wherein cyclodextrin is 2-hydroxypropyl-β-cyclodextrin (HPBCD).

4. The method of claim 1 wherein the cyclodextrin has an average molecular weight of about 900 Da to about 1500 Da.

5. The method of claim 1 wherein the PEG is PEG-400.

6. The method of claim 1 wherein the formulation comprises a pharmaceutically acceptable carrier.

7. The method of claim 6 wherein the pharmaceutically acceptable carrier comprises dimethyl sulfoxide (DMSO), dimethyl formamide (DMF), dihydrolevoglucosenone (CYRENE), γ-butyrolactone (GBL), N-methyl-2-pyrrolidone (NMP), dimethylacetamide (DMAc), or ethanol.

8. The method of claim 1 wherein the cyclodextrin is present in an amount of about 20% to about 40% w/w of the composition.

9. The method of claim 1 wherein the amount of PEG is about 20% to about 45% w/w of the composition.

10. The method of claim 8 wherein the cyclodextrin is present in an amount of about 40% w/w and the polyethylene glycol (PEG) is present in an amount of about 45% w/w.

11. The method of claim 10 wherein the cyclodextrin is 2-hydroxypropyl-β-cyclodextrin (HPBCD) and the PEG is PEG-400.

12. The method of claim 1 wherein the neurogenesis further comprises one or more of a 3-fold to about a 4-fold increase in Sox2 expression, about a 1-fold to about a 2-fold increase in Sox4 expression, about a 1-fold to about a 3.5-fold increase in Nestin expression, or about a 1-fold to about a 2.5-fold increase in DCX expression, in neural progenitor cells in treated subjects compared to subjects treated only with a PEG as the active agent.

13. The method of claim 1 wherein the administration is intramuscular (IM), subcutaneous (SC), intravenous (IV) or intrathecal.

14. A method for treating Kabuki Syndrome in a subject consisting of:
    administering intrathecally to the central nervous system of a subject a therapeutically effective amount of a composition consisting essentially of a cyclodextrin present in an amount of about 13% to about 45% w/w and a polyethylene glycol (PEG) present in an amount greater than 8% w/w, thereby treating the Kabuki Syndrome in the subject.

15. A composition consisting of:
    i) about 25% to about 45% w/w cyclodextrin; and
    ii) about 20% to about 45% w/w polyethylene glycol (PEG).

16. The composition of claim 15 wherein the cyclodextrin is 2-hydroxypropyl-β-cyclodextrin (HPBCD) and the PEG is PEG-400, and optionally, the composition further consists of a pharmaceutically acceptable carrier.

17. The method of claim 1, wherein the composition consists of:
    i) about 25% to about 45% w/w cyclodextrin;

ii) about 20% to about 45% w/w polyethylene glycol (PEG); and iii) about 10% to about 55% of a pharmaceutically acceptable carrier.

* * * * *